(12) United States Patent
Inoue et al.

(10) Patent No.: US 8,569,486 B2
(45) Date of Patent: *Oct. 29, 2013

(54) ORGANOMETAL COMPLEX AND LIGHT-EMITTING ELEMENT USING THE SAME

(75) Inventors: Hideko Inoue, Atsugi (JP); Satoshi Seo, Kawasaki (JP); Satoko Shitagaki, Atsugi (JP); Hiroko Abe, Setagaya (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/609,970

(22) Filed: Sep. 11, 2012

(65) Prior Publication Data

US 2013/0001473 A1    Jan. 3, 2013

Related U.S. Application Data

(60) Division of application No. 13/048,980, filed on Mar. 16, 2011, now Pat. No. 8,278,444, which is a division of application No. 11/797,532, filed on May 4, 2007, now Pat. No. 7,915,409, which is a division of application No. 11/023,043, filed on Dec. 28, 2004, now Pat. No. 7,238,806, which is a continuation of application No. PCT/JP2004/018079, filed on Nov. 29, 2004.

(30) Foreign Application Priority Data

Dec. 2, 2003 (JP) ................................ 2003-403822

(51) Int. Cl.
C07F 7/00 (2006.01)
(52) U.S. Cl.
USPC ........................................................ 544/225
(58) Field of Classification Search
USPC ........................................................ 544/225
See application file for complete search history.

(56) References Cited

U.S. PATENT DOCUMENTS

| | | |
|---|---|---|
| 6,303,238 B1 | 10/2001 | Thompson et al. |
| 6,565,994 B2 | 5/2003 | Igarashi |
| 6,734,457 B2 | 5/2004 | Yamazaki et al. |
| 6,780,528 B2 | 8/2004 | Tsuboyama et al. |
| 6,821,645 B2 | 11/2004 | Igarashi et al. |
| 6,821,646 B2 | 11/2004 | Tsuboyama et al. |
| 6,835,469 B2 | 12/2004 | Kwong et al. |
| 6,911,271 B1 | 6/2005 | Lamansky et al. |
| 6,939,624 B2 | 9/2005 | Lamansky et al. |
| 6,949,878 B2 | 9/2005 | Suzuri et al. |
| 6,953,628 B2 | 10/2005 | Kamatani et al. |
| 7,094,477 B2 | 8/2006 | Kamatani et al. |
| 7,147,935 B2 | 12/2006 | Kamatani et al. |
| 7,220,495 B2 | 5/2007 | Tsuboyama et al. |
| 7,238,437 B2 | 7/2007 | Igarashi et al. |
| 7,238,806 B2 | 7/2007 | Inoue et al. |
| 7,339,317 B2 | 3/2008 | Yamazaki |
| 7,355,340 B2 | 4/2008 | Shitagaki et al. |
| 7,381,479 B2 | 6/2008 | Lamansky et al. |
| 7,400,087 B2 | 7/2008 | Yamazaki |
| 7,413,816 B2 | 8/2008 | Inoue et al. |
| 7,473,575 B2 | 1/2009 | Yamazaki et al. |
| 7,482,451 B2 | 1/2009 | Thompson et al. |
| 7,482,626 B2 | 1/2009 | Yamazaki et al. |
| 7,553,560 B2 | 6/2009 | Lamansky et al. |
| 7,652,283 B2 | 1/2010 | Inoue et al. |
| 7,737,437 B2 | 6/2010 | Yamazaki et al. |
| 7,771,844 B2 | 8/2010 | Inoue et al. |
| 7,795,429 B2 | 9/2010 | Inoue et al. |
| 7,811,677 B2 | 10/2010 | Ohsawa et al. |

(Continued)

FOREIGN PATENT DOCUMENTS

| | | |
|---|---|---|
| EP | 1 191 612 | 3/2002 |
| EP | 1 348 711 | 10/2003 |

(Continued)

OTHER PUBLICATIONS

European Search Report (Application No. 04799935.4) dated Jan. 23, 2009.

(Continued)

*Primary Examiner* — Brian McDowell
(74) *Attorney, Agent, or Firm* — Eric J. Robinson; Robinson Intellectual Property Law Office, P.C.

(57) ABSTRACT

An organometallic complex according to the present invention comprises a structure represented by the following general formula (1). In the formula, $R^1$ to $R^5$ are any one selected from the group consisting of hydrogen, a halogen element, an acyl group, an alkyl group, an alkoxy group, an aryl group, a cyano group, and a heterocyclic group, Ar is an aryl group having an electron-withdrawing group or a heterocyclic group having electron-drawing group, and M is an element of Group 9 or an element of Group 10.

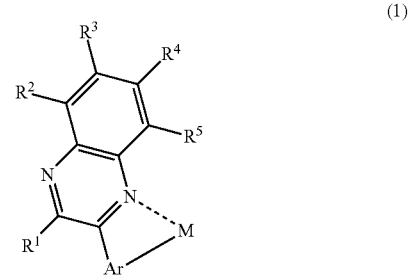

(1)

36 Claims, 10 Drawing Sheets

(56) References Cited

U.S. PATENT DOCUMENTS

| | | | |
|---|---|---|---|
| 7,915,409 B2 | 3/2011 | Inoue et al. |
| 7,939,821 B2 | 5/2011 | Inoue et al. |
| 7,951,471 B2 | 5/2011 | Inoue et al. |
| 8,227,600 B2 | 7/2012 | Inoue et al. |
| 2001/0019782 A1 | 9/2001 | Igarashi et al. |
| 2002/0034659 A1 | 3/2002 | Nishi et al. |
| 2002/0068190 A1 | 6/2002 | Tsuboyama et al. |
| 2003/0072964 A1 | 4/2003 | Kwong et al. |
| 2003/0197183 A1 | 10/2003 | Grushin et al. |
| 2003/0218418 A9 | 11/2003 | Sato et al. |
| 2004/0102632 A1 | 5/2004 | Thompson et al. |
| 2004/0230061 A1 | 11/2004 | Seo et al. |
| 2005/0003232 A1 | 1/2005 | Shitagaki et al. |
| 2005/0065342 A1 | 3/2005 | Shitagaki et al. |
| 2005/0191527 A1 | 9/2005 | Fujii et al. |
| 2006/0078758 A1 | 4/2006 | Lin |
| 2006/0240278 A1 | 10/2006 | Hatwar et al. |
| 2007/0037010 A1 | 2/2007 | Vestweber et al. |
| 2008/0076922 A1 | 3/2008 | Inoue et al. |
| 2008/0113216 A1 | 5/2008 | Inoue et al. |
| 2009/0033209 A1 | 2/2009 | Seo et al. |
| 2010/0044689 A1 | 2/2010 | Nishimura et al. |
| 2010/0237342 A1 | 9/2010 | Yamazaki et al. |
| 2011/0001133 A1 | 1/2011 | Inoue et al. |
| 2011/0024732 A1 | 2/2011 | Ohsawa et al. |
| 2011/0196152 A1 | 8/2011 | Inoue et al. |

FOREIGN PATENT DOCUMENTS

| | | |
|---|---|---|
| EP | 1 349 435 | 10/2003 |
| EP | 1 574 514 | 9/2005 |
| EP | 1 690 866 | 8/2006 |
| EP | 2 336 143 A | 6/2011 |
| JP | 63-159856 | 7/1988 |
| JP | 06-207169 | 7/1994 |
| JP | 11-329729 | 11/1999 |
| JP | 2000-231988 | 8/2000 |
| JP | 2001-247859 | 9/2001 |
| JP | 2003-040873 | 2/2003 |
| JP | 2003-058473 | 2/2003 |
| JP | 2004-155728 | 6/2004 |
| JP | 2005-239648 | 9/2005 |
| JP | 2005-298483 | 10/2005 |
| JP | 2006-073992 | 3/2006 |
| JP | 2006-182775 | 7/2006 |
| JP | 3810789 | 8/2006 |
| TW | 201100523 | 1/2011 |
| WO | WO 00/70655 | 11/2000 |
| WO | WO 01/41512 | 6/2001 |
| WO | WO 02/15645 | 2/2002 |
| WO | WO 02/45466 | 6/2002 |
| WO | WO 03/033617 | 4/2003 |
| WO | WO2004/056839 | 7/2004 |
| WO | WO 2005/054261 | 6/2005 |
| WO | WO 2005/115061 | 12/2005 |
| WO | WO2006/059802 | 6/2006 |
| WO | WO2006/104177 | 10/2006 |

OTHER PUBLICATIONS

European Office Action (Application No. 10173304.6) dated Mar. 12, 2012.

Fujii et al., *Efficient Red Organometallic Phosphors Bearing 2,3-Diphenylquinoxalines and their Application to Electrophosphorescent Diodes*, Korea-Japan Joint Forum, Organic Materials for Electronics and Photonics, Nov. 3-6, 2004, 04-O.

Tsutsui et al., *High Quantum Efficiency in Organic Light-Emitting Devices with Iridium-Complex as a Triplet Emissive Center*, Japanese Journal of Applied Physics, vol. 38, Part. 2, No. 12B, Dec. 15, 1999, pp. L1502-L1504.

O'Brien et al., *Improved Energy Transfer in Electrophosphorescent Devices*, Applied Physics Letters, vol. 74, No. 3, Jan. 18, 1999, pp. 442-444.

Baldo et al., *High-Efficiency Fluorescent Organic Light-Emitting Devices Using a Phosphorescent Sensitizer*, Nature, vol. 403, Feb. 17, 2000, pp. 750-753.

Tsutsui, *The Operation Mechanism and the Light Emission Efficiency of the Organic EL Element*, Textbook of the $3^{rd}$ Workshop of Molecular Electronic and Bioelectronics (1993), pp. 31-37.

Thompson et al., *Phosphorescent Materials and Devices*, Proceedings of the $10^{th}$ International Workshop on Inorganic and Organic Electroluminescence (EL'00), Dec. 4-7, 2000, pp. 35-38.

Duan et al., *New Iridium Complexes as Highly Efficient Orange-Red Emitters in Organic Light-Emitting Diodes*, Adv. Mater, vol. 15, No. 3, Feb. 5, 2003, pp. 224-228.

Ito et al., *Living Polymerization of 1,2-Diisocyanoarenes Promoted by (Quinoxalinyl)nickel Complexes*, Polymer Journal, vol. 24, No. 3, 1992, pp. 297-299.

Lewis, Hawley's Condensed Chemical Dictionary, $12^{th}$ et., Van Nostrand Reinhold, 1993, p. 594.

Jakubke et al., Concise Encyclopedia Chemistry, Walter de Gruyter & Co., 1993, p. 490.

Parker, McGraw-Hill Dictionary of Chemical Terms, $3^{rd}$ edition, McGraw-Hill, Inc., 1985, p. 200.

Ito et al., *Asymmetric Synthesis of Helical Poly(quinoxaline-2,3-diyl)s by Palladium-Mediated Polymerization of 1,2-Diisocyanobenzenes: Effective Control of the Screw-Sense by a Binaphthyl Group at the Chain-End*, Journal of the American Chemical Society, vol. 120, 1998, pp. 11880-11893.

English Translation of International Search Report & Written Opinion for Application No. PCT/JP2004/018079 (except front page) dated Apr. 5, 2005.

Kulikova et al., *Effects of the Nature of the Ligand Environment and Metal Center on the Optical and Electrochemical Properties of Platinum(II) and Palladium(II) Ethylenediamine Complexes with Heterocyclic Cyclometalated Ligands*, Russian Journal of General Chemistry, vol. 70, No. 2, Feb. 2000, pp. 163-170.

Balashev et al., *Synthesis and Properties of Palladium(II) and Platinum(II) (2,3-diphenylquinoxalinato-C,N) ethylenediamine Complexes*, Russian Journal of General Chemistry, vol. 69, No. 8, Aug. 1999, pp. 1348-1349.

Steel et al., *Cyclometallated Compounds, V\*. Double Cyclopalladation of Diphenyl Pyrazines and Related Ligands*, Journal of Organometallic Chemistry, vol. 395, No. 3, 1990, pp. 359-373.

Rasmussen et al., *Synthesis and Characterization of a Series of Novel Rhodium and Iridium Complexes Containing Polypyridyl Bridging Ligands: Potential Uses in the Development of Multimetal Catalysts for Carbon Dioxide Reduction*, Inorganic Chemistry, vol. 29, No. 20, 1990, pp. 3926-3932.

Zhang et al., *Synthesis and Photoluminescence of a New Red Phosphorescent Iridium(III) Quinoxaline Complex*, Chinese Chemical Letters, vol. 15, No. 11, Nov. 12, 2004, pp. 1349-1352.

Fujii et al., *Highly Efficient and Vivid-Red Phosphors Bearing 2,3-Diphenylquinoxaline Units and Their Application to Organic Light-Emitting Devices*, IEICE Trans. Electron., vol. E87-C, No. 12, Dec. 2004, pp. 2119-2121.

Tsutsui et al., "Electroluminescence in Organic Thin Films," Photochemical Processes in Organized Molecular Systems, 1991, pp. 437-450.

Baldo et al., "Highly Efficient Phosphorescent Emission from Organic Electroluminescent Devices," Nature, Sep. 10, 1998, vol. 395, pp. 151-154.

Baldo et al., "Very High-Efficiency Green Organic Light-Emitting Devices Based on Electrophosphorescence," Appl. Phys. Lett. (Applied Physics Letters), Jul. 5, 1999, vol. 75, No. 1, pp. 4-6.

Nishi et al., "High Efficiency TFT-OLED Display with Iridium-Complex as Triplet Emissive Center," Proceedings of the $10^{th}$ International Workshop on Inorganic and Organic Electroluminescence (EL'00), Dec. 4, 2000, pp. 353-356.

Tang et al., Appl. Phys. Lett. (Applied Physics Letters), "Organic Electroluminescent Diodes," Sep. 21, 1987, vol. 51, No. 12, pp. 913-915.

Seo et al., "P-132: Long-Lived Deeply Red Phosphorescent OLEDs Based on Electrochemically Stable Ir Complexes," SID Digest '05, SID International Symposium Digest of Technical Papers, vol. 36, 2005, pp. 806-809.

(56) References Cited

OTHER PUBLICATIONS

Yamamoto et al., "Preparation of New Electron-Accepting π-Conjugated Polyquinoxalines. Chemical and Electrochemical Reduction, Electrically Conducting Properties, and Use in Light-Emitting Diodes," J. Am. Chem. Soc. (Journal of the American Chemical Society), vol. 118, No. 16, 1996, pp. 3930-3937.
International Search Report (Application No. PCT/JP2005/009310) dated Aug. 30, 2005.
Written Opinion (Application No. PCT/JP2005/009310) dated Aug. 30, 2005.
International Search Report (Application No. PCT/JP2005/022593) dated Mar. 14, 2006.
Written Opinion (Application No. PCT/JP2005/022593) dated Mar. 14, 2006.
International Search Report (Application No. PCT/JP2005/022507) dated Feb. 21, 2006.
Written Opinion (Application No. PCT/JP2005/022507) dated Feb. 21, 2006.
Brooks et al., "Synthesis and Characterization of Phosphorescent Cyclometalated Platinum Complexes," Inorg. Chem. (Inorganic Chemistry), 2002, vol. 41, No. 12, pp. 3055-3066.
Williams et al., "Synthesis, Characterization, and DNA Binding Properties of a Series of Ru, Pt Mixed-Metal Complexes," Inorg. Chem. (Inorganic Chemistry), 2003, vol. 42, No. 14, pp. 4394-4400.
European Search Report (Application No. 10173304.6) Dated Apr. 12, 2011.
Webster's Third New International Dictionary, 1986, Merriam-Webster, Inc., Springfield, MA (SA); pp. 23, "acyl".
Parker, McGraw-Hill Dictionary of Scientific and Technical Terms, Fifth Edition, 1993, McGraw-Hill Book Company, pp. 31, "acyl".
Pine, Organic chemistry, Fifth Edition, 1987, McGraw-Hill Book Company, pp. 266-267.
Pine, Organic chemistry, Fifth Edition, 1987, McGraw-Hill Book Company, pp. 703-704.
Patani et al., "Bioisosterism: A Rational Approach in Drug Design," Chemical Reviews, vol. 96, No. 8, 1996, pp. 3147-3176. Eng.
Taiwanese Office Action (Application No. 093136922) Dated Nov. 2, 2011.
European Office Action (Application No. 10173304.6) dated Mar. 2, 2012.
Korean Office Action (Application No. 2012-7009988) dated May 10, 2012.
Taiwanese Office Action (Application No. 99128448) Dated Mar. 7, 2013.

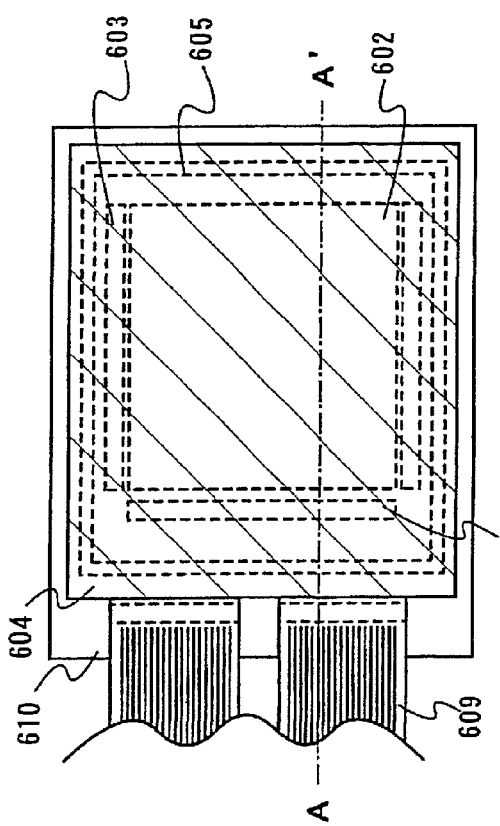
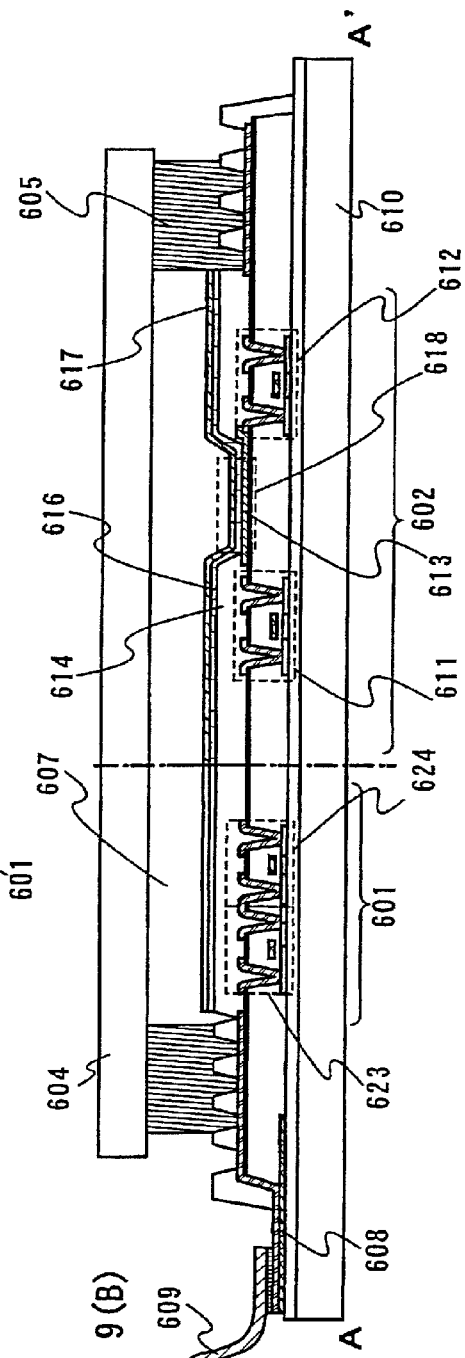
Fig. 9(A)
Fig. 9(B)

ORGANOMETAL COMPLEX AND LIGHT-EMITTING ELEMENT USING THE SAME

This application is a Divisional Application of U.S. application Ser. No. 13/048,980 filed Mar. 16, 2011; which is a Divisional Application of U.S. application Ser. No. 11/797,532 filed May 4, 2007, now U.S. Pat. No. 7,915,409; which is a Divisional Application of U.S. application Ser. No. 11/023,043 filed Dec. 28, 2004, now U.S. Pat. No. 7,238,806; which is a U.S. National Stage entry of PCT Application No. PCT/JP2004/018079, filed Nov. 29, 2004. This application also claims priority to Japanese Application Serial No. 2003-403822 filed Dec. 2, 2003.

TECHNICAL FIELD

The present invention relates to a novel organometallic complex, and more particularly relates to an organometallic complex that is capable of converting a triplet excited state into luminescence. Further, the present invention relates to a light-emitting element that has an anode, a cathode, and a layer including an organic compound (hereinafter, referred to as "a layer including a luminescent material") from which luminescence can be obtained by applying an electric field.

BACKGROUND ART

An organic compound (organic molecule) gets to have energy (excited state) by absorbing light. Through the excited state, various reactions (photochemical reactions) and luminescence may be generated, and are used for various applications.

As an example of photochemical reactions, there is a reaction of a singlet oxygen with an unsaturated organic molecular (oxygenation) (for example, refer to Non-Patent Reference 1). Oxygen in a singlet state (singlet oxygen) is not be generated by direct photoexcitation since the ground state of an oxygen molecule is a triplet excited state. However, in the presence of other triplet excited molecules, singlet oxygen is generated to enable an oxygenation reaction. In this case, a compound capable of forming the triplet excited molecules is referred to as a photosensitizer.

As mentioned above, a photosensitizer capable of forming triplet excited molecules by photoexcitation is necessary for generating singlet oxygen. However, the ground state of an organic compound is normally a singlet ground state. Thus, a photoexcitation to a triplet excited state is a forbidden transition and a triplet excited molecular is unlikely to be generated (a singlet excited molecular is normally generated). Therefore, for such a photosensitizer, a compound in which intersystem crossing from a singlet excitation state to a triplet excitation state tends to occur (alternatively, a compound which allows a forbidden transition of photoexcitation directly to a triplet excited state) is required. That is to say, it is possible and effective to use such a compound a photosensitizer.

In addition, such a compound can often emit phosphorescence. Phosphorescence is luminescence generated by the transition between energy states that are different in multiplicity, and in the case of a common organic compound, indicates luminescence generated in returning from a triplet excited state to a singlet ground state (on the other hand, luminescence generated in returning from a singlet excited state returns to a singlet ground state is referred to as fluorescence). Application fields of a compound capable of emitting luminescence, that is, a compound capable of converting a triplet excited state into luminescence (hereinafter, referred to as "phosphorescent compound") includes an light-emitting element using an organic compound as a luminescent compound.

The light-emitting element has characteristics such as slimness and lightweight, high-speed response, direct-current low-voltage driving. Therefore, the light-emitting element is a device attracting attention as the next-generation flat-panel display element. In addition, since the visibility is relatively favorable due to light emission by itself and a wide viewing angle, the light-emitting element is considered to be effective as element to be used for a display screen of a portable device.

In the case of using an organic compound as a light emitter, the emission mechanism of the light-emitting element is included a carrier-injection type. Namely, when a voltage is applied to electrodes with a light-emitting layer interposed therebetween, an electron injected from a cathode and a hole injected from an anode are recombined in the light-emitting layer to form an excited molecule, and energy is released to emit light when the excited molecule returns to the ground state.

In addition, as the type of the excited molecule, an excited singlet state (S*) and an excited triplet state (T*) are possible as in the case of the above-mentioned photoexcitation. In addition, it is believed that the statistical generation ratio in the case of the light emitting element is $S^*:T^*=1:3$ (for example, refer to Non-Patent Reference 2).

However, in the case of a common organic material, luminescence (phosphorescence) from a triplet excited state is not observed at room temperature, and normally, only luminescence (fluorescence) from a singlet excited state is observed. This is because the ground state of an organic compound is normally a singlet ground state ($S_0$), and thus, $T^* \rightarrow S_0$ transition (phosphorescence process) is a strongly forbidden transition and $S^* \rightarrow S_0$ transition (fluorescence process) is an allowed transition.

Accordingly, in the case of the light-emitting element, the theoretical limit of the internal quantum efficiency (the ratio of generated photons to injected carriers) is considered to be 25% on the ground of $S^*:T^*=1:3$.

However, $T^* \rightarrow S_0$ transition (phosphorescence process) is allowed when the phosphorescent compound is used, and thus, the internal quantum efficiency can be 75% to 100% theoretically. Namely, the luminous efficiency can be 3 to 4 times as high as a conventional luminous efficiency. In fact, light-emitting elements using phosphorescence compounds have been released one after another, and the luminous efficiency has been attracting attention (for example, refer to Non-Patent Reference 3 and Non-Patent Reference 4).

In Non-Patent Reference 3, a porphyrin complex with platinum as a central metal is used, and in Non-Patent Reference 4, an organometallic complex with iridium as a central metal is used. The complexes are both phosphorescent compounds.

In addition, by alternately stacking a layer including an organometallic complex with iridium as a central material (hereinafter, referred to as "iridium complex") and a layer including DCM2 that is a known fluorescent compound, it is possible that triplet excitation energy generated in the iridium complex is transferred to DCM2 to contribute to the luminescence of DCM2 (for example, refer to Non-Patent Reference 5). In this case, since the amount of singlet excited state of DCM2 (normally, 25% or less) is amplified more than usual, the luminous efficiency of DCM2 is increased. This can be said to be also sensitization of the iridium complex, which is a phosphorescent compound.

As shown in Non-Patent Reference 3 to Non-Patent Reference 5, a light-emitting element using a phosphorescent compound can achieve a higher luminous efficiency than ever before (namely, less current makes it possible to achieve a higher luminous efficiency). Therefore, it is considered that the light-emitting element using the phosphorescent compound will give greater importance in the future development as a method for achieving luminescence with a higher luminance and a high luminous efficiency.

As described above, a phosphorescent compound tends to be occurred intersystem crossing and to generate luminescence (phosphorescence) from a triplet excited state. Therefore, the phosphorescent compound is an expected compound since the phosphorescent compound is useful for using as a photosensitizer and for applying to a light-emitting element as a phosphorescent material. However, the current state is that the number of photophorescent compounds is small.

As one of the few the phosphorescent compounds, the iridium complex used in Non-Patent Reference 4 or Non-Patent Reference 5 is one of organometallic complexes referred to as an orthometalated complex. The complex has a lifetime of several hundreds nanoseconds, and a high phosphorescent quantum yield. Therefore, since the decrease in efficiency due to increase in luminance is small as compared with the above-mentioned porphyrin complex, the complex is effective in a light-emitting element. Also in that way, such an organometallic complex is one of guidances for synthesizing a compound in which direct photoexcitation to a triplet excited state and intersystem crossing tend to occur, consequently a phosphorescent compound.

The structure of a ligand of the iridium complex used in Non-Patent Reference 4or Non-Patent Reference 5 is relatively simple and shows green luminescence with favorable color purity. However, the structure of the ligand needs to be changed to change the luminescent color to other colors. For example, in Non-Patent Reference 6, various ligands and iridium complexes using the ligands are synthesized, and some luminescent colors are realized.

However, many of the ligands have difficulty in being synthesized or have many steps required for synthesizing, which leads to price increases of materials themselves. In these organometallic complexes, though it is often the case that iridium or platinum is used as a central metal to emit phosphorescence, these metals themselves are expensive, and additionally, the ligands also become expensive. In addition, blue luminescence with favorable color purity has not been realized.

Further, in Non-Patent reference 7, an iridium complex using dibenzo[f, h]quinoxialine derivative as a ligand is synthesized. A light-emitting element using those shows orange-red luminescence with a high efficiency. Red luminescence with favorable color purity has not been realized.

In addition, an organometallic complex is easily decomposed commonly. Even in the case of an organometallic complex which is awkward to be decomposed, the thermal decomposition temperature thereof is never high. Namely, an organometallic complex is poor in heat resistance, which becomes problem in applying to an electronic device as a light-emitting element.

The descriptions above show the necessity to synthesize an organometallic complex that is excellent in also heat resistance with the use of a ligand which is capable of being synthesized easily and changing a luminescent color to other colors. This is because inexpensive and various photosensitizers and phosphorescent materials (that is, materials in which intersystem crossing to a triplet excited state tends to occur) can be obtained.

Non-Patent Reference 1: Haruo INOUE, and three others, Basic Chemistry Course PHOTOCHEMISTRY I (Maruzen Co., Ltd.), 106-11

Non-Patent Reference 2: Tetsuo TSUTSUI, Textbook for the 3$^{rd}$ Workshop, Division of Molecular Electronics and Bio-electronics, Japan Society of Applied Physics, 31 (1993)

Non-Patent Reference 3: D. F. O'Brien, and three others, Applied Physics Letters, vol. 74, No. 3, 442-444 (1999)

Non-Patent Reference 4: Tetsuo TSUTSUI, and eight others, Japanese Journal of Applied Physics, vol. 38, L1502-L1504 (1999)

Non-Patent reference 5: M. A. Baldo, and two others, Nature (London), vol. 403, 750-753 (2000)

Non-Patent Reference 6: Mark E. Thompson, and ten others, The 10$^{th}$ International workshop on Inorganic and Organic Electroluminescence (EL' 00), 35-38

Non-Patent Reference 7: J. Duan, and two others, Advanced Materials (2003), 15, No. 3, FEB5

DISCLOSURE OF INVENTION

Problem to be Solved by the Invention

It is an object of the present invention to provide a novel organometallic complex in which intersystem crossing to a triplet excited state tends to occur by using a ligand that is high in quantum efficiency and that is easily synthesized. In addition, particularly, it is an object of the present invention to provide a novel organometallic complex that is excellent in heat resistance.

Further, it is an object of the present invention to provide a light-emitting element that is high in heat resistance and color purity by manufacturing the light-emitting element with the use of the organometallic complex. Furthermore, it is an object of the present invention to provide a light-emitting device with low power consumption by manufacturing the light-emitting device with the use of the light-emitting element.

It is to be found that an organometallic complex forming a structure represented by a following general formula (1) can emit phosphorescence by present inventors as a result of the examination diligently.

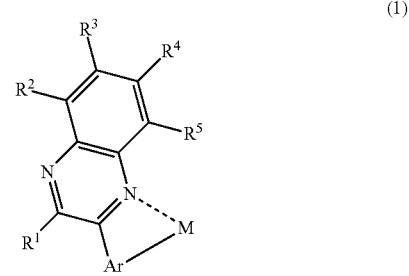

(1)

(In the formula, each of $R^1$ to $R^5$ is any one selected from the group consisting of hydrogen, a halogen element, an acyl group, an alkyl group, an alkoxy group, an aryl group, a cyano group, and a heterocyclic group, Ar is an aryl group having an electron-withdrawing group or a heterocyclic group having electron-drawing group, and M is an element of Group 9 or an element of Group 10.)

Accordingly, an aspect of the present invention provides an organometallic complex including the structure represented by the general formula (1).

In particular, an organometallic complex including a structure represented by the following general formula (2) is preferable.

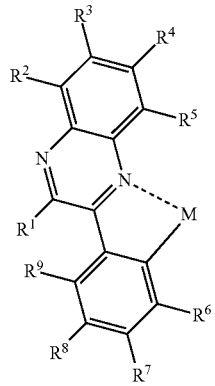

(2)

(In the formula, each of $R^1$ to $R^5$ is any one selected from the group consisting of hydrogen, a halogen element, an acyl group, an alkyl group, an alkoxy group, an aryl group, a cyano group, and a heterocyclic group, at least one of $R^6$ to $R^9$ is an electron-withdrawing group, further, each of $R^6$ to $R^9$ is any one selected from the group consisting of hydrogen, a halogen element, an acyl group, an alkyl group, an alkoxy group, an aryl group, a cyano group, and a heterocyclic group, and M is an element of Group 9 or an element of Group 10.)

It has been found that an organometallic complex represented by the following general formula (3) is capable of emitting phosphorescence.

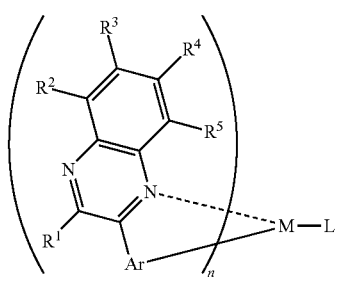

(3)

(In the formula, each of $R^1$ to $R^5$ is any one selected from the group consisting of hydrogen, a halogen element, an acyl group, an alkyl group, an alkoxy group, an aryl group, a cyano group, and a heterocyclic group, Ar is an aryl group having an electron-withdrawing group or a heterocyclic group having electron-drawing group, M is an element of Group 9 or an element of Group 10, n=2 when the M is the element of Group 9 while n=1 when the M is the element of Group 10, and L is any one of a monoanionic ligand having a β-diketone structure, a monoanionic bidentate ligand having a carboxyl group, and a monoanionic bidentate ligand having a phenolic hydroxyl group.)

Accordingly, an aspect of the present invention provides an organometallic complex represented by the general formula (3). Particularly, an organometallic complex represented by the following general formula (4) is preferable.

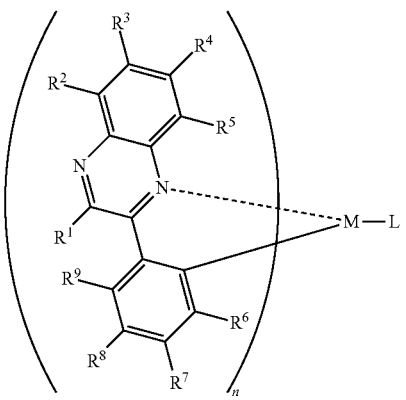

(4)

(In the formula, each of $R^1$ to $R^5$ is any one selected from the group consisting of hydrogen, a halogen element, an acyl group, an alkyl group, an alkoxy group, an aryl group, a cyano group, and a heterocyclic group, at least one of $R^6$ to $R^9$ is an electron-withdrawing group, further, each of $R^6$ to $R^9$ are any one selected from the group consisting of hydrogen, a halogen element, an acyl group, an alkyl group, an alkoxy group, an aryl group, a cyano group, and a heterocyclic group, M is an element of Group 9 or an element of Group 10, n=2 when the M is the element of Group 9 while n=1 when the M is the element of Group 10, and L is any one of a monoanionic ligand having a β-diketone structure, a monoanionic bidentate ligand having a carboxyl group, and a monoanionic bidentate ligand having a phenolic hydroxyl group.)

Further, while the ligand L can be one of a monoanionic ligand having a β-diketone structure, a monoanionic bidentate ligand having a carboxyl group, and a monoanionic bidentate ligand having a phenolic hydroxyl group in each of the general formula (1) to (4), it is preferable that the ligand L is any one of monoanionic ligands shown by the following structure formulas (5) to (11). The monoanionic ligands which have high coordination ability and are inexpensively available are effective.

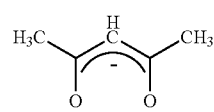

(5)

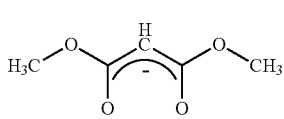

(6)

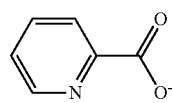

(7)

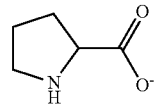

(8)

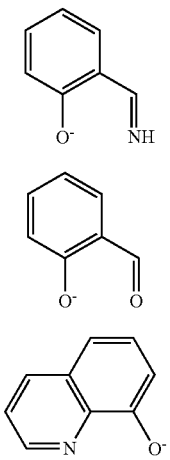

(9)

(10)

(11)

In addition, in the organometallic complex including the structure represented by the general formula (1) or (2), or the organometallic complex represented by the general formula (3) or (4), it is preferable that the electron-withdrawing group be any one of a halogen group, and a haloalkyl group. These electron-withdrawing groups are effective since it becomes possible to improve the chromaticity adjustment and the internal quantum efficiency of the organometallic complex including the structure represented by the general formula (1) or (2), or the organometallic complex represented by the general formula (3) or (4).

Further, in the organometallic complex including the structure represented by the general formula (1) or (2), or the organometallic complex represented by the general formula (3) or (4), it is preferable that the electron-withdrawing group be a fluoro group or a trifluoromethyl group. The fluoro group is the trifluoromethyl, which has a high Further, it has been found by the inventors that an organometallic complex including a structure represented by the following general formula (12) is capable of emitting phosphorescence.

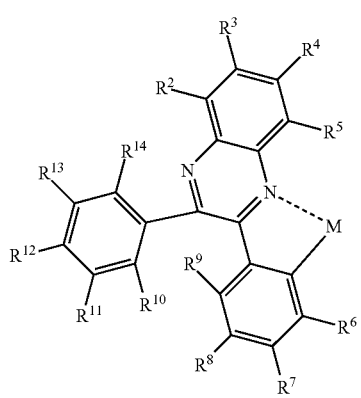

(12)

(In the formula, each of $R^2$ to $R^{14}$ is any one selected from the group consisting of hydrogen, a halogen element, an acyl group, an alkyl group, an alkoxy group, an aryl group, a cyano group, and a heterocyclic group, and M is one of an element of Group 9 or an element of Group 10.)

Accordingly, an aspect of the present invention provides an organometallic complex including the structure represented by the general formula (12). Particularly, an organometallic complex including a structure represented by the following general formula (13) is preferable.

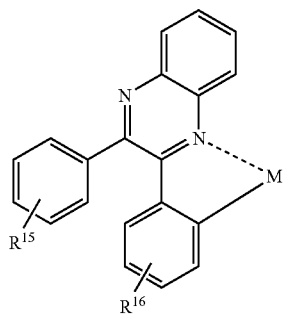

(13)

(In the formula, $R^{15}$ or $R^{16}$ is any one selected from the group consisting of hydrogen, a halogen element, and a haloalkyl group, and M is an element of Group 9 or an element of Group 10.)

Further, particularly, it has been found by the inventors that an organometallic complex represented by a following general formula (14) is capable of emitting phosphorescence.

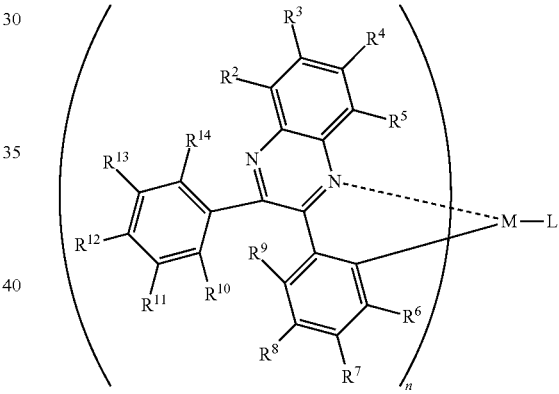

(14)

(In the formula, each of $R^2$ to $R^{14}$ is any one selected from the group consisting of hydrogen, a halogen element, an acyl group, an alkyl group, an alkoxy group, an aryl group, a cyano group, and a heterocyclic group, M is an element of Group 9 or an element of Group 10, n=2 when the M is the element of Group 9 while n=1 when the M is the element of Group 10, and L is any one of a monoanionic ligand having a β-diketone structure, a monoanionic bidentate ligand having a carboxyl group, and a monoanionic bidentate ligand having a phenolic hydroxyl group.)

Accordingly, an aspect of the present invention provides an organometallic complex represented by the general formula (14).

In addition, in the general formula (14), while the ligand L can be one of a monoanionic ligand having a β-diketone structure, a monoanionic bidentate ligand having a carboxyl group, and a monoanionic bidentate ligand having a phenolic hydroxyl group, it is preferable that the ligand L be any one of monoanionic ligands shown by the following structure formulas (5) to (11) These monoanioc bidentate ligands, which have high coordination ability and are inexpensively available, are effective.

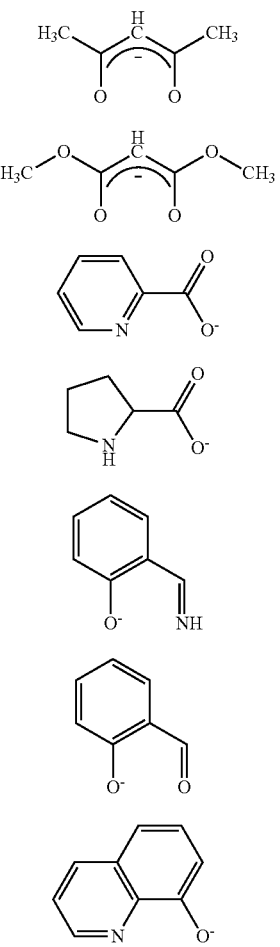

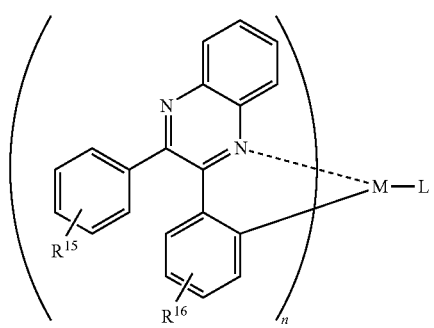

(In the formula, $R^{15}$ or $R^{16}$ is any one selected from the group consisting of hydrogen, a halogen element, and a haloalkyl group, M is an element of Group 9 or an element of Group 10, n=2 when the M is the element of Group 9 while n=1 when the M is the element of Group 10, and L is any one of a monoanionic ligand having a β-diketone structure, a monoanionic bidentate ligand having a carboxyl group, and a monoanionic bidentate ligand having a phenolic hydroxyl group.)

In addition, in the general formula (15), while the ligand L can be one of a monoanionic ligand having a β-diketone structure, a monoanionic bidentate ligand having a carboxyl group, and a monoanionic bidentate ligand having a phenolic hydroxyl group, it is preferable that the ligand L is any one of monoanionic ligands shown by the following structure formulas (5) to (11). The monoanioc bidentate ligands, which have high coordination ability and are inexpensively available, are effective.

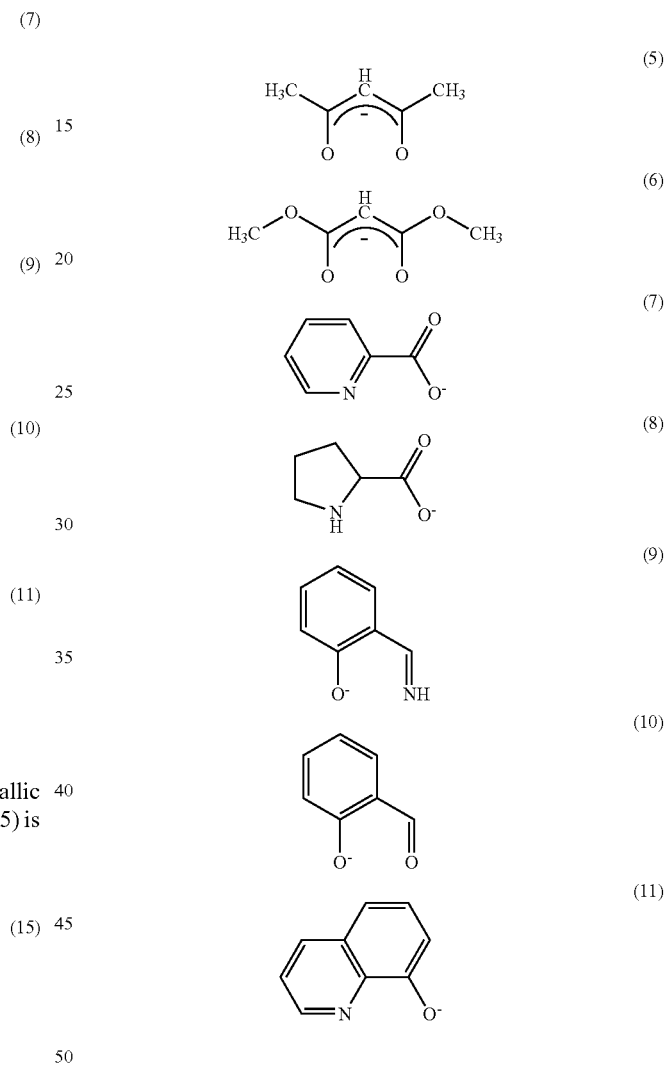

In addition, in the organometallic complex including the structure represented by the general formula (12), the organometallic complex represented by the general formula (14), or the organometallic complex where the ligand L in the organometallic complex represented the general formula (14) that is any one of the monoanionic bidenta ligands shown by the following structures (5) to (10), it is preferable that one of $R^6$ to $R^9$ be an electron-withdrawing group. Since the organometallic complex including the structure represented by the general formula (12), the organometallic complex represented by the general formula (14), or the organometallic complex where the ligand L in the organometallic complex represented the general formula (14) that is any one of the monoanionic bidenta ligands shown by the following structures (5) to (10) is capable of emitting stronger phosphorescence, these electron-withdrawing groups are effective.

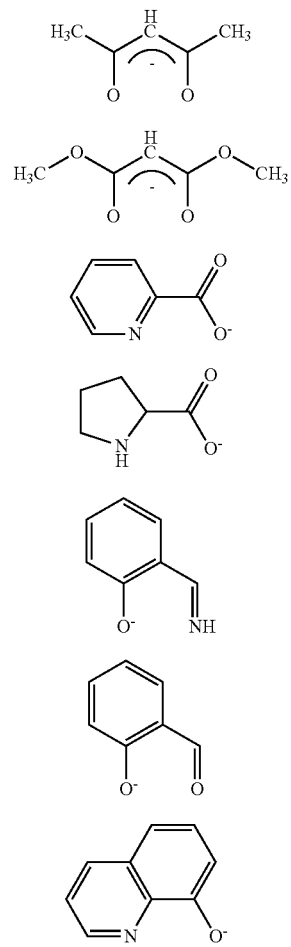

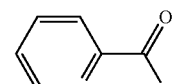
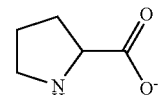
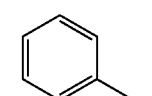
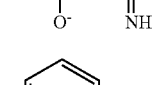
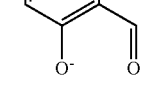

In addition, in the organometallic complex including the structure represented by the general formula (13), the organometallic complex represented by the general formula (15), or the organometallic complex where the ligand L in the organometallic complex represented the general formula (15) that is any one of the monoanionic bidenta ligands shown by the following structures (5) to (10), it is preferable that $R^{15}$ or $R^{16}$ be an electron-withdrawing group. The organometallic complex including the structure represented by the general formula (13), the organometallic complex represented by the general formula (15), or the organometallic complex where the ligand L in the organometallic complex represented the general formula (15) that is any one of the monoanionic bidenta ligands shown by the following structures (5) to (10) is capable of emitting stronger, these electron-withdrawing groups, are effective.

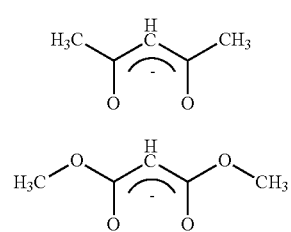

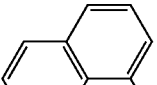
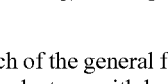
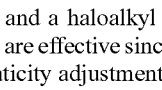
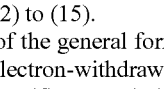
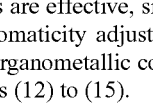
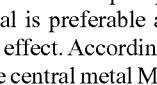
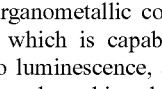

In addition, in each of the general formulas (12) to (15), it is preferable that the electron-withdrawing group be any one of a halogen group and a haloalkyl group. These electron-withdrawing groups are effective since it becomes possible to improve the chromaticity adjustments and the quantum efficiencies of the organometallic complexes represented by the general formulas (12) to (15).

Further, in each of the general formulas (12) to (15), it is preferable that the electron-withdrawing group be any one of a fluoro group and a trifluoromethyl group. These electron-withdrawing groups are effective, since it becomes possible to improve the chromaticity adjustments and the quantum efficiencies of the organometallic complexes represented by the general formulas (12) to (15).

In addition, in order to emit phosphorescence more effectively, a heavy metal is preferable as a central metal in the light of heavy atom effect. Accordingly the present invention has a feature that the central metal M is iridium or platinum in each of the general formula (1) to (4) and (12) to (15).

And now, the organometallic complex according to the present invention, which is capable of converting triplet excited energy into luminescence, are quite effective since higher efficiency can be achieved by applying to a light-emitting element. Therefore, the present invention includes a light-emitting element using the organometallic complex according to the present invention.

In this case, while the organometallic complex according to the present invention may be used as a sensitizer as described in Non-Patent Reference 6, it is more effective in terms for luminous efficiency to use the organometallic complex according to the present invention as a light emitter described as in Non-Patent Reference 5. Therefore, the present invention has a feature of a light-emitting element using the organometallic complex as a light emitter.

In particular, a light-emitting element to which a light-emitting layer using the organometallic complex according to the present invention as a guest material and using a quinoxaline derivative as a host material is applied is preferable.

In addition, since the thus obtained light-emitting element according to the present invention can achieve a high luminous efficiency, a light-emitting device (an image display device and a luminous device) using this light-emitting element can achieve low power consumption. Therefore, the present invention includes a light-emitting device using the light-emitting element according to the present invention.

It is noted to be that the light-emitting device in this specification indicates an image display or the luminous device using a light-emitting element that has a layer including a luminescent material between a pair of electrodes as a light-emitting element. Further, a module in which a connector, for example, an anisotropic conductive film, TAB (Tape Automated Bonding) tape, or TCP (Tape Carrier Package) is attached to the light-emitting device, a module set a printed wiring board is provided at the tip of a TAB tape or TCP, or a module in which an IC (integrated circuit) is directly mounted on the light-emitting device by a COG (Chip On Glass) method is all included in the light-emitting device Effect of the Invention By implementing the present invention, a novel organometallic complex in which intersystem crossing to a triplet excited tends to occur can be obtained. In addition, a light-emitting element that is novel favorable heat resistance can be obtained by manufacturing a light-emitting element with the use of the organometallic complex according to the present invention. Further, a light-emitting device with low power consumption can be obtained by manufacturing the light-emitting device using the light-emitting element.

BRIEF DESCRIPTION OF DRAWINGS

In the accompanying drawings:

FIGS. 9A-9B are diagrams illustrating a light-emitting device;

BEST MODE FOR CARRYING OUT THE INVENTION

Figure 1:
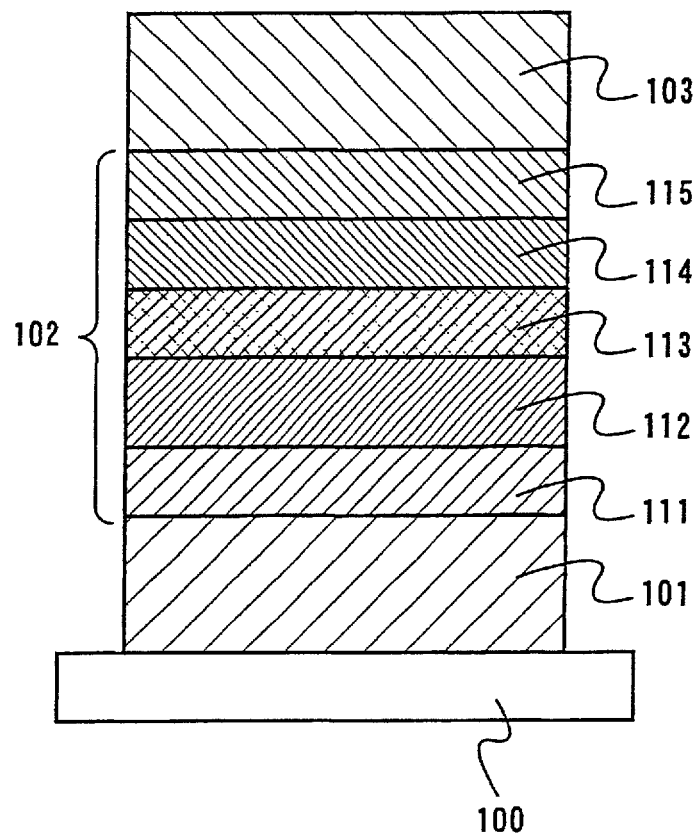
FIG. 1 is a diagram illustrating the structure of a light-emitting element using an organometallic complex according to the present invention.

An organometallic complex according to the present invention can be obtained by orthometallation of a ligand shown by the following general formula (16).

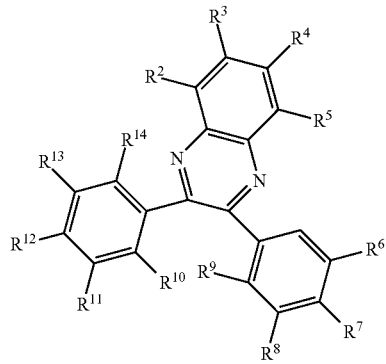

(In the formula, $R^2$ to $R^{14}$ are any one selected from the group consisting of hydrogen, a halogen element, an acyl group, an alkyl group, an alkoxy group, an aryl group, a cyano group, and a heterocyclic group.)

It is to be noted that a ligand represented by the general formula (16) can be synthesized, in accordance with the following synthesis scheme (17).

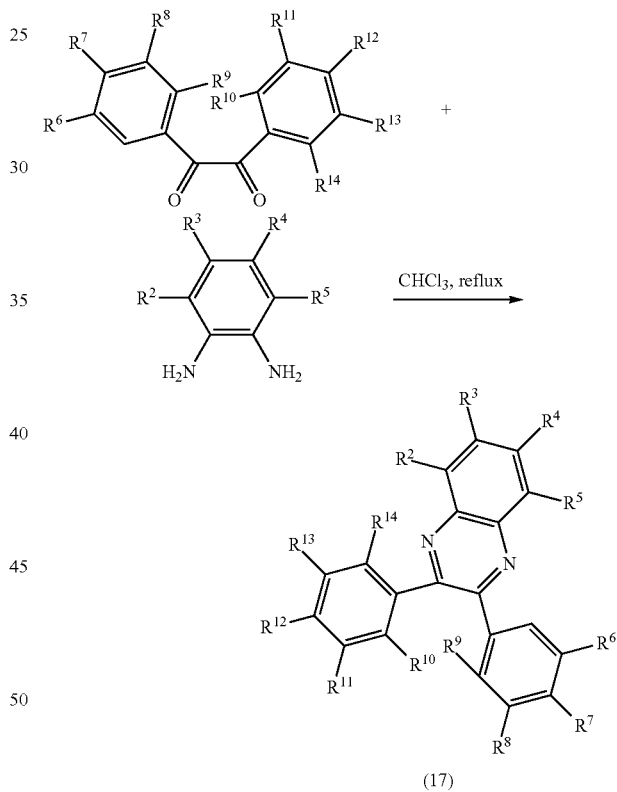

The thus obtained ligand represented by the general formula (16) is used to form an orthometalated complex that is an organometallic complex according to the present invention. The common synthesis method may be used for orathometallation in this case.

For example, when an organometallic complex with iridium as a central metal according to the present invention is synthesized, a chloro-bridged dinuclear complex is first synthesized with the use of iridium chloride hydrate as a raw material for the central metal by mixing the iridium chloride hydrate with the ligand represented by the general formula (16) and holding the iridium chloride hydrate mixed with the ligand at reflux in a nitrogen atmosphere (the following synthesis scheme (18)).

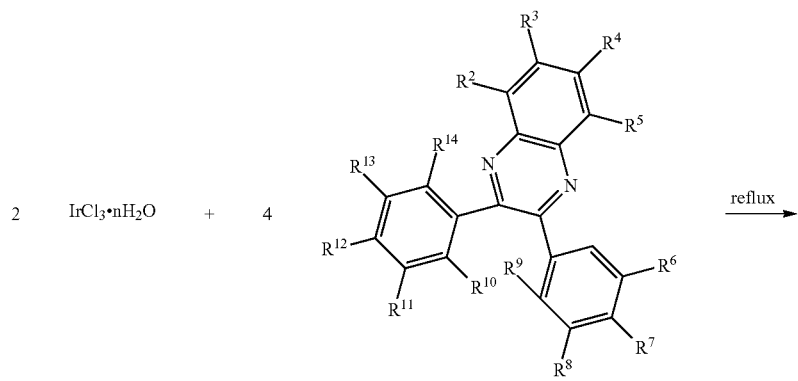
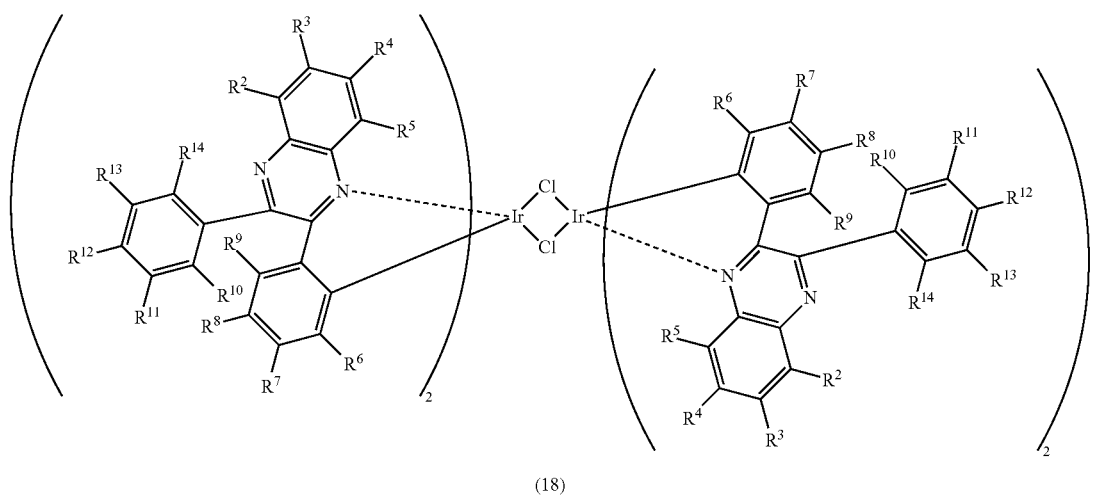
(18)
Next, by mixing the obtained dinuclear complex with a ligand L and holding the dinuclear complex mixed with the ligand L at reflux in a nitrogen atmosphere, the chlorine bridge is cut with the ligand L to obtain an organometallic complex according to the present invention (the following synthesis scheme (19)).
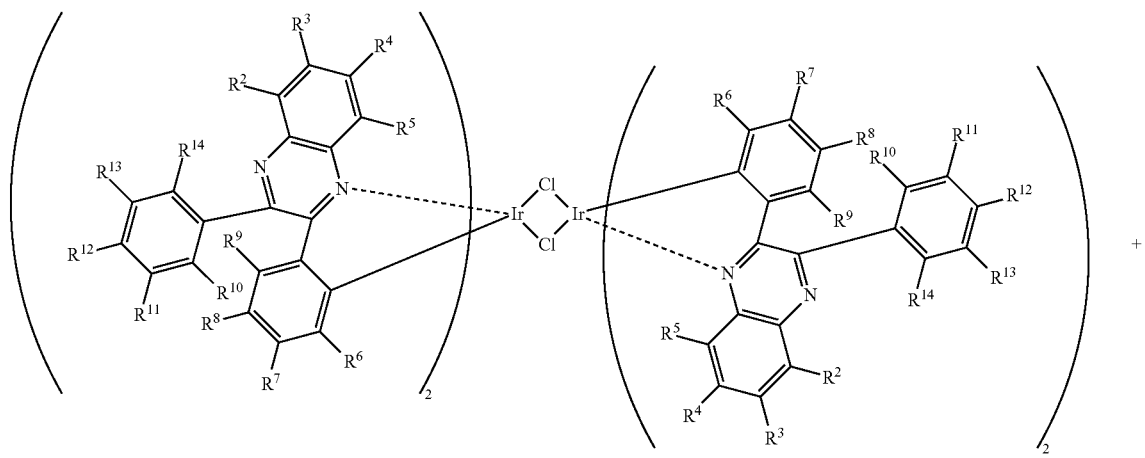

 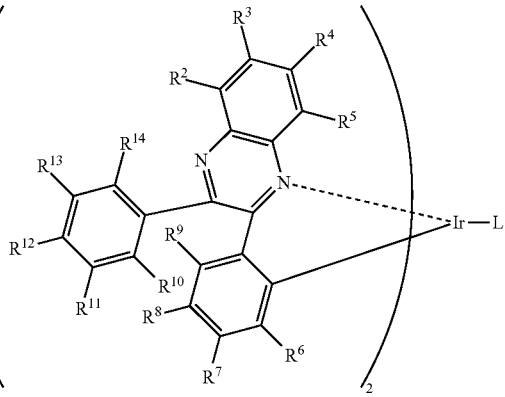

(19)

It is to be noted that the synthesis method of an organometallic complex according to the present invention is not to be considered limited to the synthesis method described above.

The thus obtained organometallic complex according to the present invention has a carrier transporting property since a qionoxaline derivative that has an electron transporting property is used as a ligand. Therefore, it is possible to use the organometallic complex according to the present invention for an electron device. In addition, by changing the structure of the ligand represented by the general formula (16), characteristics such as various luminescent colors can be obtained. Specific examples thereof include the following structure formulas (20) to (59), for example. However, an organometallic complex according to the present invention is not to be considered limited to the organometallic complexes.

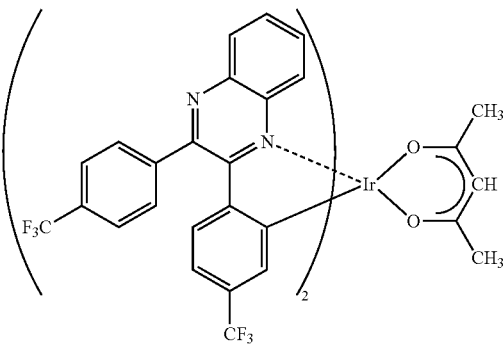

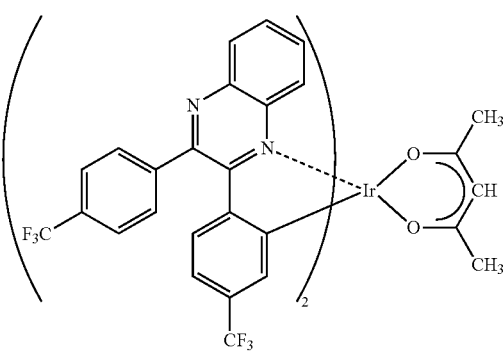

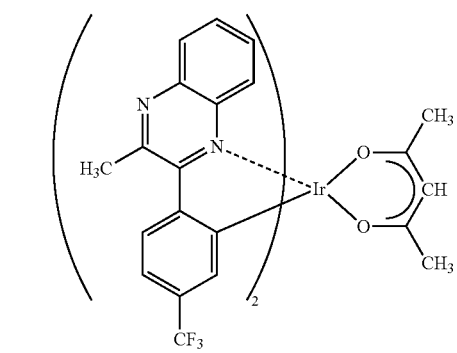

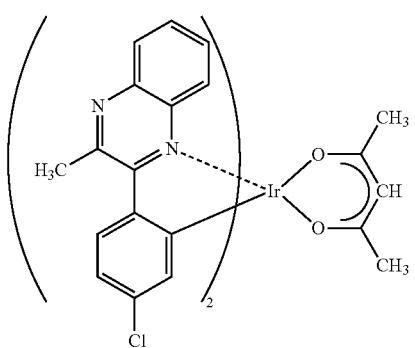
(25)
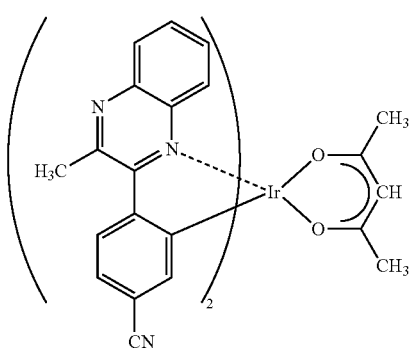
(26)
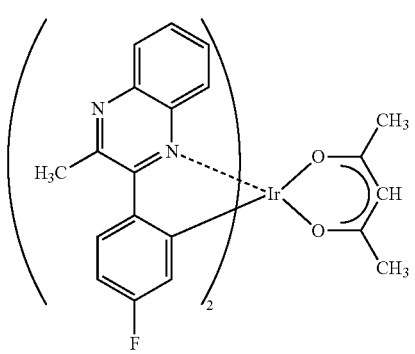
(27)
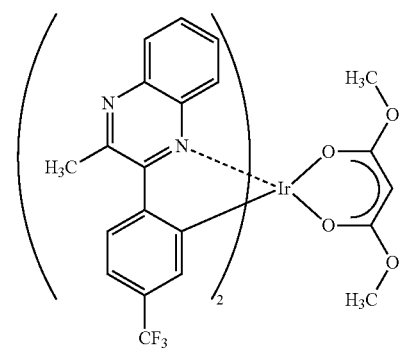
(28)
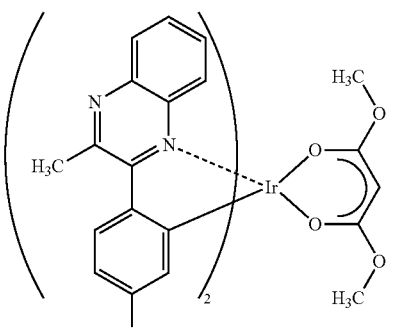
(29)
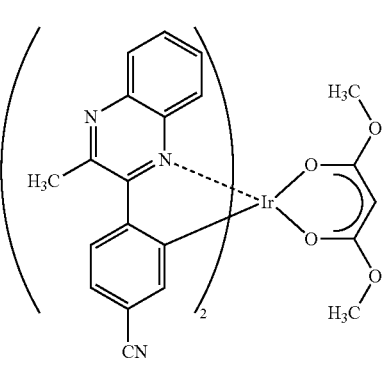
(30)
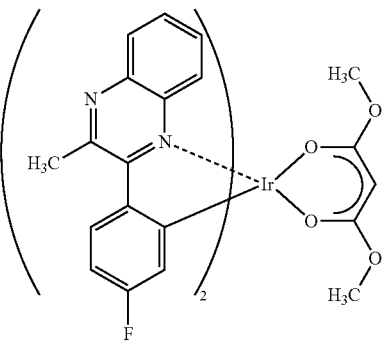
(31)
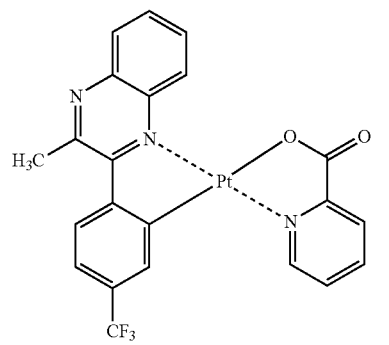
(32)

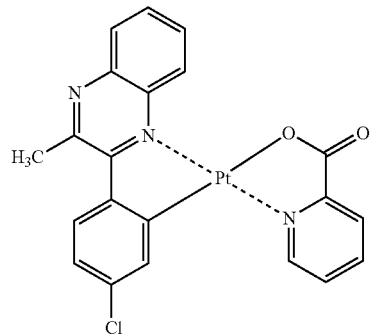
(33)
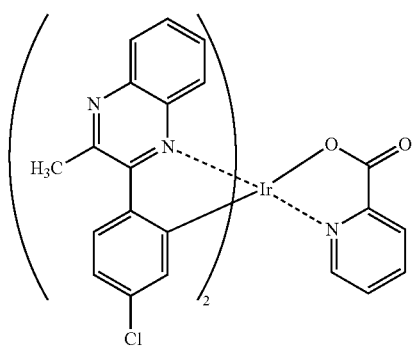
(37)
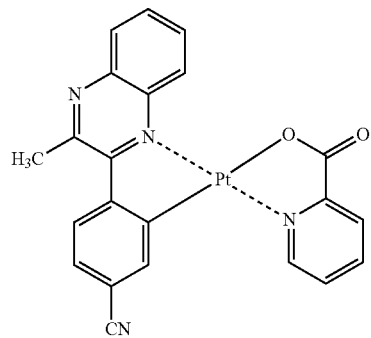
(34)
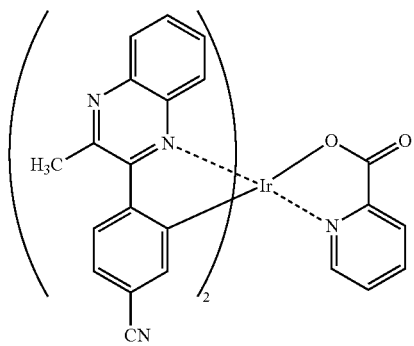
(38)
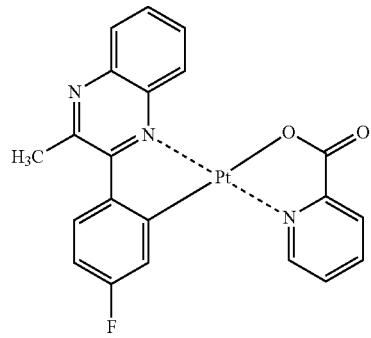
(35)
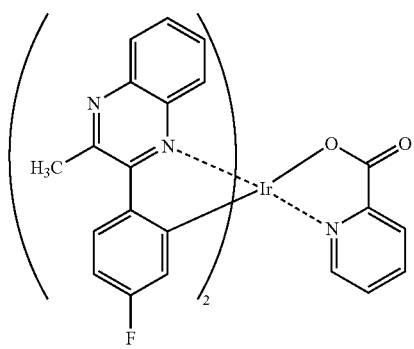
(39)
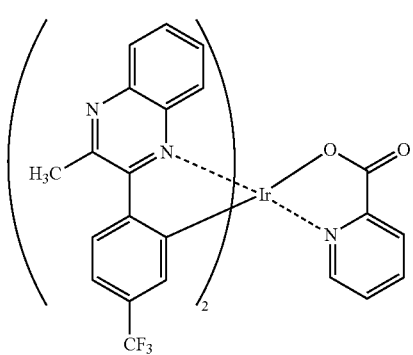
(36)
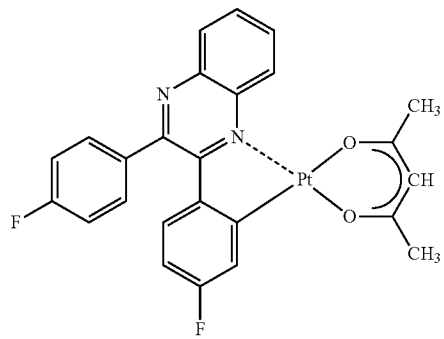
(40)

(41)
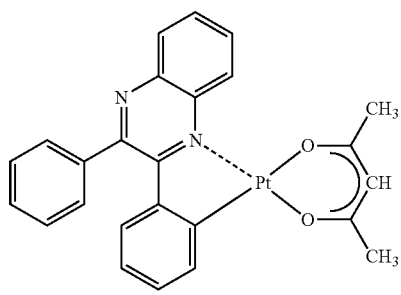
(42)
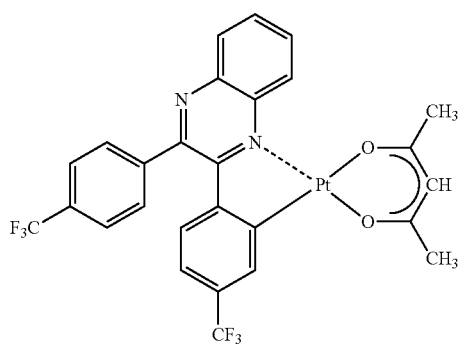
(43)
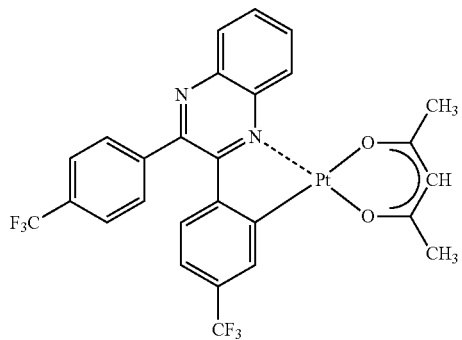
(44)
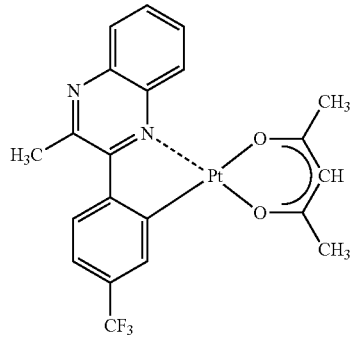
(45)
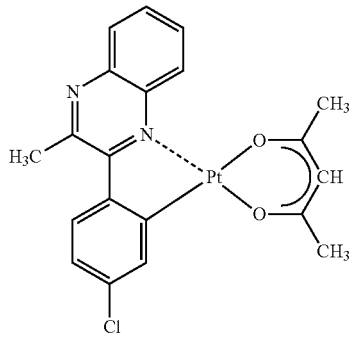
(46)
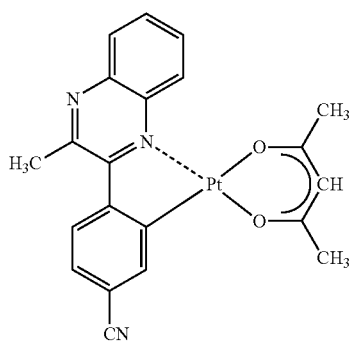
(47)
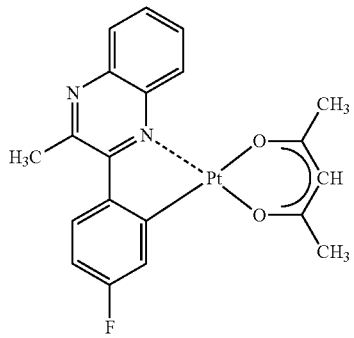
(48)
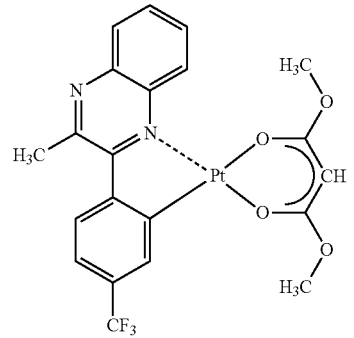

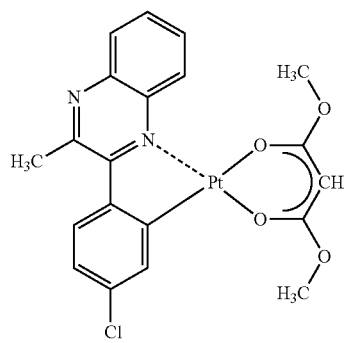
(49)
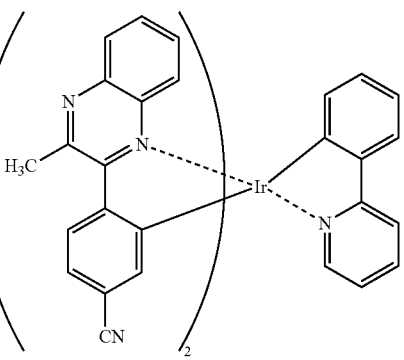
(54)
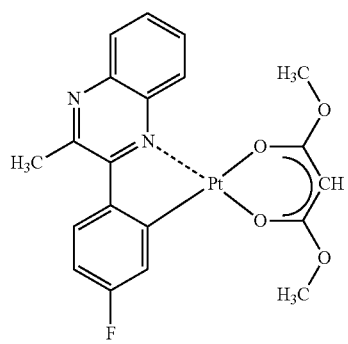
(51)
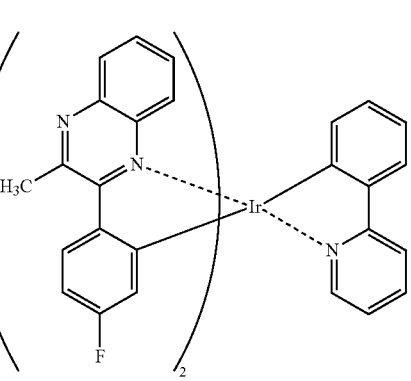
(55)
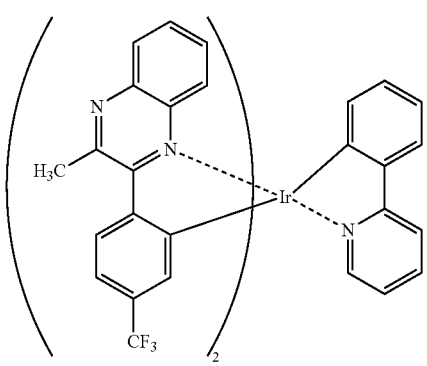
(52)
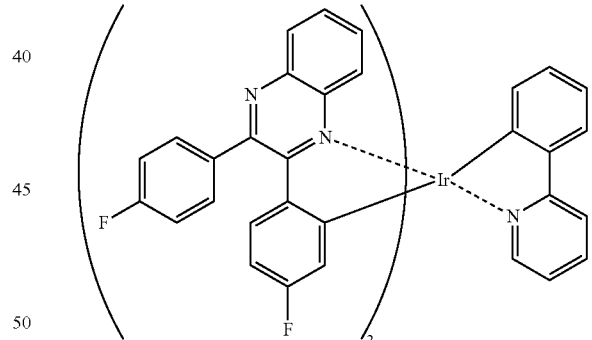
(56)
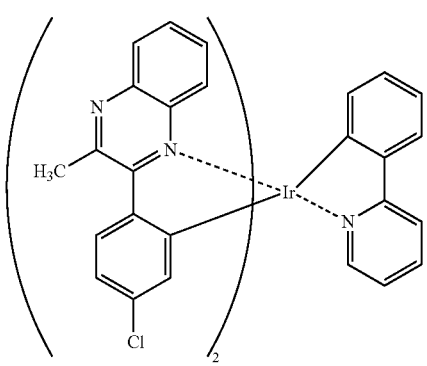
(53)
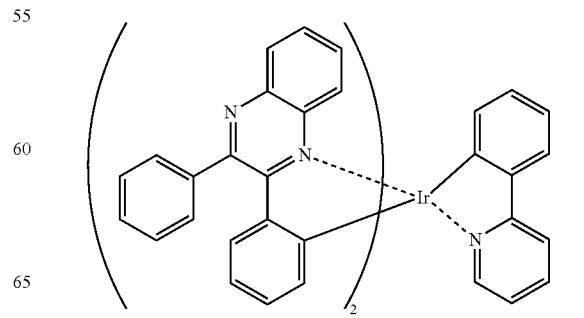
(57)

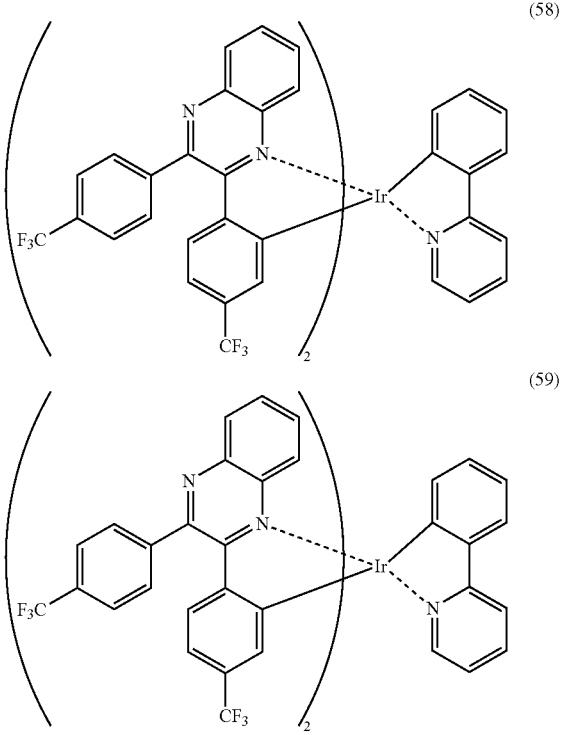

The organometallic complex according to the present invention can be used as a luminous sensitizer and a phosphorescent material. A mode of applying the organometallic complex according to the present invention to a light-emitting element will be described below.

A light-emitting element according to the present invention basically has an element structure in which a light-emitting layer (such as a hole injecting layer, a hole transporting layer, a light-emitting layer, a hole blocking layer, an electron transporting layer, or an electron injecting layer) including the above mentioned organometallic complex according to the present invention (the organometallic complex including the structure composed of the general formula (1), (2), (12), and (13), or the above general formula (3), (4), (14), and (15)) is interposed between a pair of electrodes (an anode and a cathode).

In addition, as materials except the organometallic complex according to the present invention, which is used for the light-emitting layer, the known materials may be used and any of low molecular weight materials and polymer materials can be used. Further, materials for forming the light-emitting layer include not only a material composed of only an organic compound material but also a structure including an inorganic compound as a part.

Embodiments of light-emitting elements according to the present invention will be described in detail below.

[Embodiment 1]

In Embodiment 1, the structure of a light-emitting element that has a light-emitting layer including the organometallic complex according to the present invention, and has a hole injection layer, a hole transporting layer, a hole blocking layer, and an electron transporting layer composed of low molecular weight materials will be described with reference to FIG. 1.

In FIG. 1, the light-emitting element according to the present invention has a structure in which a first electrode 101 is formed on a substrate 100, a layer 102 including a luminescent material is formed on the first electrode 101, and a second electrode 103 is formed thereon.

As a material to be used for the substrate 100 here, a material that is used for a conventional light-emitting element may be used. For example, glass, quartz, transparent plastic, and a flexible substrate can be used.

In addition, the first electrode 101 and the second electrode 103 in Embodiment mode 1 function as an anode and a cathode, respectively.

Namely, the first electrode 101 is formed by using an anode material. As the anode material that can be used here, it is preferable to use a metal, an alloy, an electrically conductive compound, and a mixture thereof, which have a larger work function (a work function of 4.0 eV or more). As specific examples of the anode material, gold (Au), platinum (Pt), nickel (Ni), tungsten (W), chromium (Cr), molybdenum (Mo), iron (Fe), cobalt (Co), copper (Cu), or palladium (Pd), and a nitride of a metal material TiN, or the like can be used in addition to ITO (indium tin oxide), ITSO (indium tin silicon oxide), and IZO (indium zinc oxide) of indium oxide mixed with 2 to 20% zinc oxide (ZnO).

On the other hand, as a cathode material to be used for the second electrode 103, it is preferable to use a metal, an alloy, an electrically conductive compound, and a mixture thereof, which have a smaller work function (a work function of 3.8 eV or less). As specific examples of the cathode material, in addition to elements belonging to Group 1 or 2 of the periodic table of the elements, that is, alkali metals such as Li and Cs and alkali-earth metals such as Mg, Ca, and Sr, and an alloys (Mg:Ag or Al:Li) and compounds (LiF, CsF, and $CaF_2$) including these, a transition metal including a rare-earth metal can be used to form the second electrode 103. The second electrode 103 can be formed also by using a lamination layer of the cathode material and a metal (including an alloy) such as Al, Ag, or ITO.

A thin film composed of the above-mentioned anode material and a thin film composed of the above-mentioned cathode material are formed by a method such as evaporation or sputtering to form the first electrode 101 and the second electrode 103 respectively. It is preferable that the film thickness be 10 to 500 nm. Finally, a protective layer (a barrier layer) composed of an inorganic material such as SiN or an organic material such as Teflon (registered trademark) or a styrene polymer is formed. The barrier layer may be transparent or non-transparent, and the inorganic material or organic material is formed by a method such as evaporation or sputtering.

Further, a desiccant such as SrOx or SiOx is formed by a method such as electron beam irradiation, evaporation, sputtering, or a sol-gel method to save an organic layer and an electrode of the light-emitting layer from oxidation and the moisture.

In the light-emitting element according to the present invention, light generated by recombination of carriers in a light-emitting layer is emitted from one or both of the first electrode 101 and the second electrode 103 to the outside. Namely, the first electrode 101 is formed by using a light-transmitting material when the light is emitted from the first electrode 101 while the second electrode 103 is formed by using a light-transmitting material when the light is emitted from the second electrode 103.

The layer 102 including the luminescent material is formed by stacking a plurality of layers, in Embodiment 1, by stacking a hole injecting layer 111, a hole transporting layer 112, a light-emitting layer 113, a hole blocking layer 114, and an electron transporting layer 115.

A phthalocyanine compound is effective for a hole injecting material forming the hole injecting layer 111. For example, phthalocyanine (abbreviation: referred to as H$_2$-Pc) and copper phthalocyanine (abbreviation: referred to as Cu-Pc) can be used.

An aromatic amine compound (that is, a compound having a benzene ring-nitrogen bond) is preferable for a hole transporting material forming a hole transporting layer 112. Materials that are extensively used include, for example, in addition to 4,4'-bis[N-(3-methylphenyl)-N-phenyl-amino]-biphenyl (abbreviation: TPD), 4,4'-bis [N-(1-naphthyl)-N-phenyl-amino]-biphenyl (abbreviation: α-NPD) that is a derivative of TPD, or starburst aromatic amine compounds such as 4,4',4"-tris(N,N -diphenyl-amino)-triphenylamine (abbreviation: TDATA) and 4,4',4"-tris[N-(3-methylphenyl)-N-phenylamino]-triphenylamine (abbreviation: MTDATA). Further, a composite matcrial of material of a conductive inorganic compound such as MoOx and the organic compound can be also used.

The light-emitting layer 113 includes an organometallic compound including the structure composed of the general formulas (1), (2), (12), and, (13) or an organometallic compound represented by the general formulas (3), (4), (14), and (15) and is formed by co-evaporation of the organometallic complex and a host material. As the host material, the known materials such as 4,4'-bis(N-carbazolyl)-biphenyl (abbreviation: CBP) or 2,2',2"-(1,3,5-benzentri-yl)-tris[1-phenyl-1H-benzimidazole] (abbreviation: TPBI).

As a hole blocking material forming the hole blocking layer 114, bis(2-methyl-8-quinolinolato)-4-phenylphenolato-aluminum (abbreviation: BAlq), 1,3-bis[5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP), and the like can be used.

For an electron transporting material in the case of forming the electron transporting material 115, metal complexes having a quinoline skeleton or a benzoquinoline skeleton such as tris (8-quinolinolato) aluminum (abbreviation: Alq$_3$), tris (5-methyl-8-quinolilato) aluminum (abbreviation: Almq$_3$), and bis(10-hydroxybenzo[h]-quinolinato) beryllium (abbreviation: BeBq$_2$), and BAlq mentioned above are suitable. In addition, metal complexes having an oxazole ligand or a thiazole ligand such as bis[2-(2-hydroxyphenyl)-benzoxazolato]zinc (abbreviation: Zn(BOX)$_2$) and bis[2-(2-hydroxyphenyl)-benzothiazolato]zinc (abbreviation: Zn(BTZ)$_2$) can be also used. Further, besides the metal complexes, 2-(4-biphenylyl)-5-(4-tert-butylphenyl)-1,3,4-oxadiazole (abbreviation: PBD), and OXD-7, TAZ, p-EtTAZ, BPhen, and BCP mentioned above also can be used as the electron transporting material. Furthermore, the inorganic material such as TiOx can be also used.

As described above, the light-emitting element that has the light-emitting layer 113 including the organometallic complex according to the present invention, and the hole injecting layer 111, the hole transporting layer 112, the hole blocking layer 114 and the electron transporting layer 115, which are composed of low molecular weight materials, can be formed.

In addition, in Embodiment 1, the organometallic complex according to the present invention is used as a guest material in the light-emitting layer 113, and the light-emitting element, in which luminescence obtained from the organometallic complex according to the present invention is used for a luminescent color, is provided.

[Embodiment 2]

Figure 2:
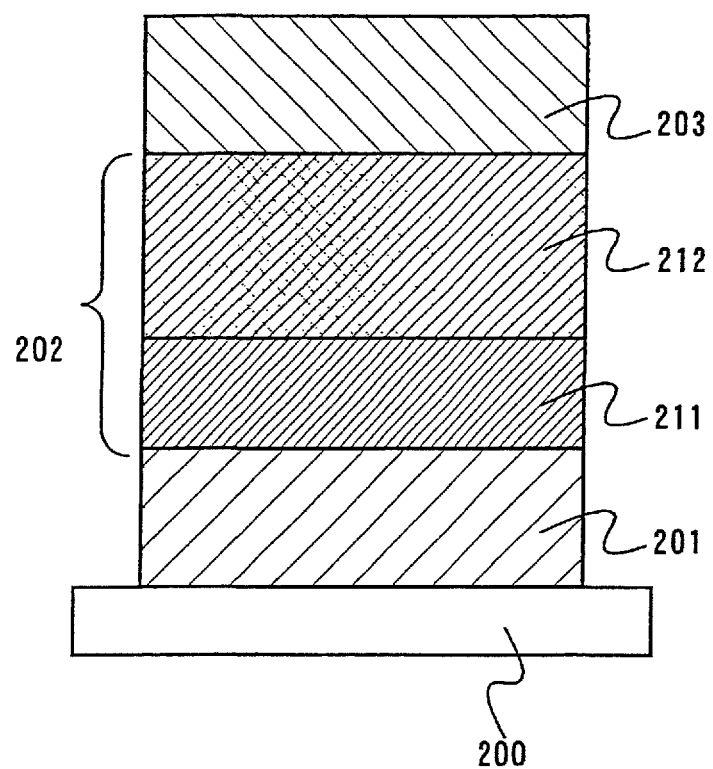
FIG. 2 is a diagram illustrating the structure of a light-emitting element using an organometallic complex according to the present invention.

In Embodiment 2, the structure of a light-emitting element that has a light-emitting layer including an organometallic complex according to the present invention and a hole injecting layer composed of a polymer material, which are formed by a wet process, will described with reference to FIG. 2.

It is noted that a substrate 201, a first electrode 201, and a second electrode 203 can be formed by using the same materials in the same way as in Embodiment 1. Therefore, descriptions thereof are omitted.

Further, a layer 202 including a luminescent material is formed by stacking a plurality of layers, in Embodiment 2, by stacking a hole injecting layer 211 and a light-emitting layer 212.

As a hole injecting material forming the hole injecting layer 211, polyethylenedioxythiophene (abbreviation: PEDOT) doped with polystyrene sulfonate (abbreviation: PSS), polyaniline, and polyvinyl carbazole (abbreviation: PVK) can be used.

The light-emitting layer 212 includes an organometallic complex including a structure composed of the general formulas (1), (2), (12), and (13) or an organometallic complex represented by the formulas (3), (4), (14), and (15) according to the present invention as a guest material. A host material may be a bipolar material, or a bipolar material may be produced by mixing a hole transporting material with an electron transporting material. Here, at first, a hole transporting polymer compound (for example, PVK) and the electron transporting material (for example, PBD) are dissolved in the same solvent at 7:3 (mole ratio), and further, a moderate amount of an organometallic complex (about 5 wt %) according to the present invention is added to prepare a solution. The light-emitting layer 212 can be obtained by wet coating of this solution.

As described above, a light-emitting element that has the light-emitting layer 212 including the organometallic complex according to the present invention and a hole injection layer 211 composed of a polymer material, which are formed by a wet process, can be obtained.

[Embodiment 3]

Figure 3:
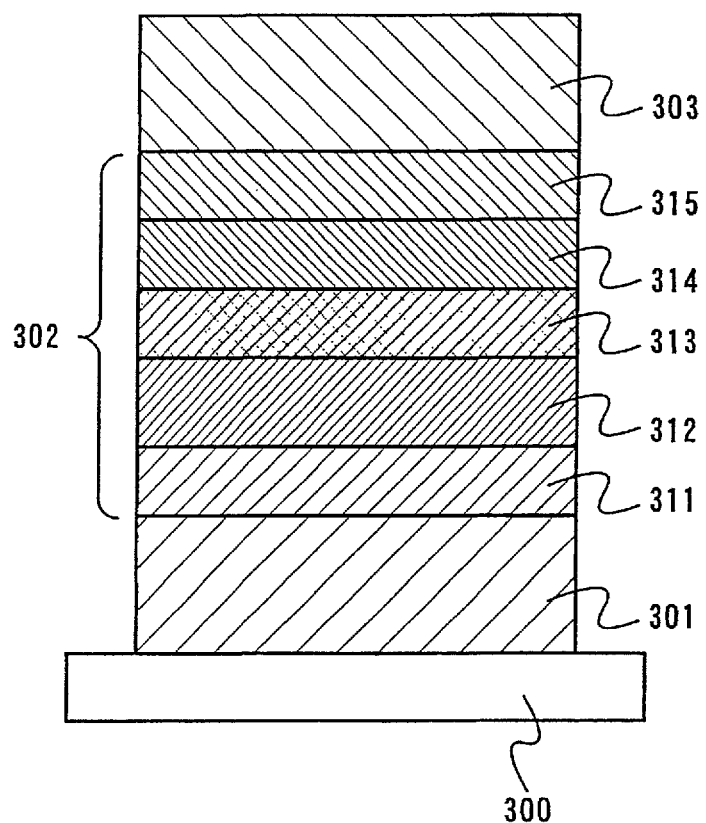
FIG. 3 is a diagram illustrating the structure of a light-emitting element using an organometallic complex according to the present invention.

In Embodiment 3, the structure of a light-emitting element that has a light-emitting layer including two kinds of materials which are an organometallic complex according to the present invention and a fluorescent compound, and a hole injecting layer, a hole transporting layer, a hole blocking layer, and an electron transporting layer which are composed of low molecular weight materials will be described with reference to FIG. 3. In FIG.3, there is a layer 302 including a luminescent material between a first electrode 301 and a second electrode 303. The layer 302 including the luminescent material is formed by stacking a hole injecting layer 311, a hole transporting layer 312, a light-emitting layer 313, a hole blocking layer 314, and an electron transporting layer 315.

It is to be noted that a substrate 300, the first electrode 301, the second electrode 303, the hole injecting layer 311, the hole transporting layer 312, the hole blocking layer 314, and the electron transporting layer 315 can be formed with the use of the same materials and in the same way as in Embodiment. Therefore, descriptions thereof are omitted.

The light-emitting layer 313 in the present embodiment is composed of a host material, an organometallic complex according to the present invention as a first guest material, and a fluorescent compound as a second guest material. As a host material, the material mentioned in Embodiment 1 can be used.

In addition, as the second guest material, known fluorescent materials can be used. Specifically, DCM1, DCM2, DCJTB, quinacridone, N, N-dimethylquinacridone, rubrene, perylene, DPT, Co-6, PMDFB, BTX, ABTX, and the like can be used.

In Embodiment 3, as in the case of Non-Patent Reference 6, the organometallic complex according to the present invention, which is the first guest material, functions as a sensitizer, and increases the number of singlet excited states of the fluorescent compound, which is the second guest material, in the light-emitting layer 313. Therefore, the light-emitting element of Embodiment 3 is a light-emitting element in which luminescence obtained from the fluorescent compound is used for a luminescent color, and further, makes the luminous efficiency of the fluorescent compound can be improved as compared to a conventional state. Further, in the light-emitting element using the organometallic complex according to the present invention, either an anode or a cathode can be stacked first.

Figure 5A:
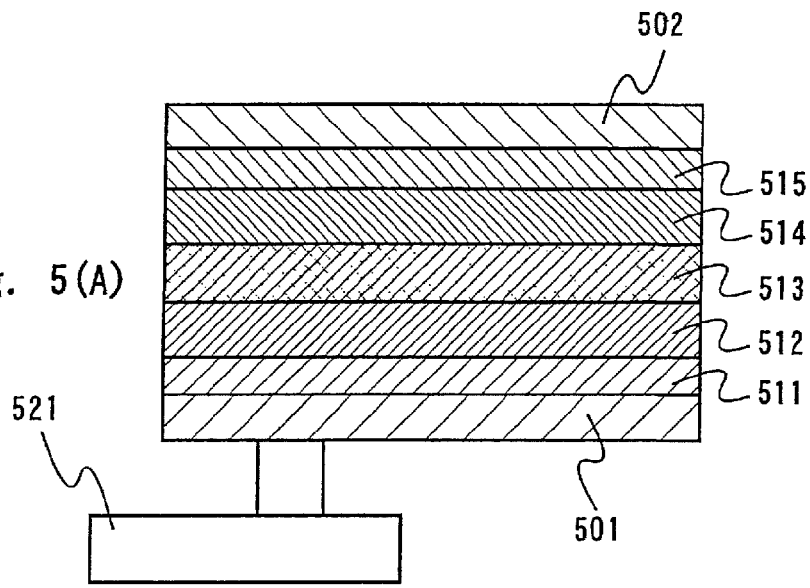
FIG. 5 is a diagram illustrating the structures of a light-emitting element according to the present invention.
Figure 5B:
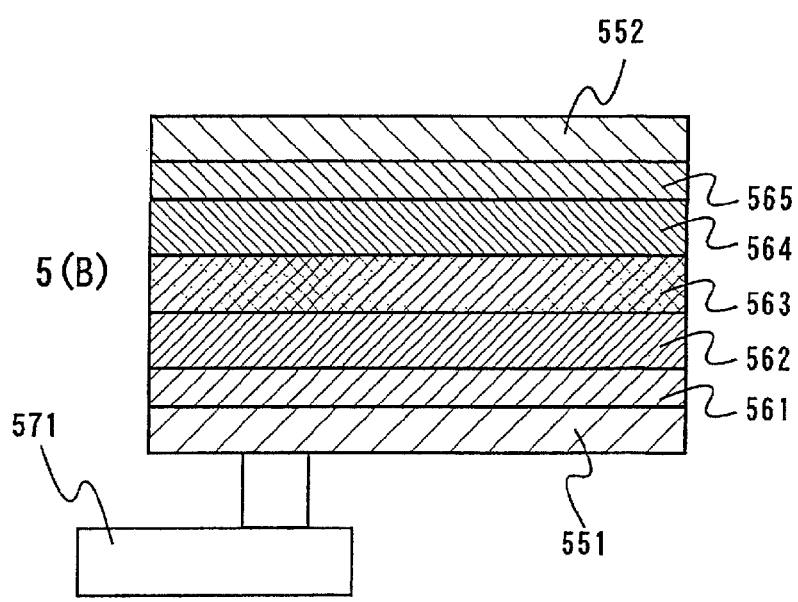

For example, FIG. 5(A) is a diagram of a light-emitting element formed by stacking an anode first, and, FIG. 5(B) is a diagram of a light-emitting element formed by stacking a cathode first. In FIG. 5(A), following an anode 501, a hole injecting layer 511/a hole transporting layer 512/a light-emitting layer 513/an electron transporting layer 514/an electron injecting layer 515/a cathode 502 are stacked in this order. Here, a p-channel TFT 521 is attached to the anode 501. Further, in FIG. 5(B), following a cathode 551, an electron injecting layer 561/an electron transporting layer 562/a light-emitting layer 563/a hole transporting layer 564/a hole injecting layer 565/an anode 552 are stacked in this order. Here, an n-channel TFT is attached to the cathode 551. In addition, in the present embodiment, a hole injecting layer, a hole transporting layer, a light-emitting layer, an electron transporting layer, and an electron injecting layer are shown as the layer including the luminescent material which is interposed between the anode and the cathode. However, there is no need for it necessarily. Supporting layers such as a hole blocking layer and a mixed layer can be formed.

[Embodiment 4]

Figure 4:
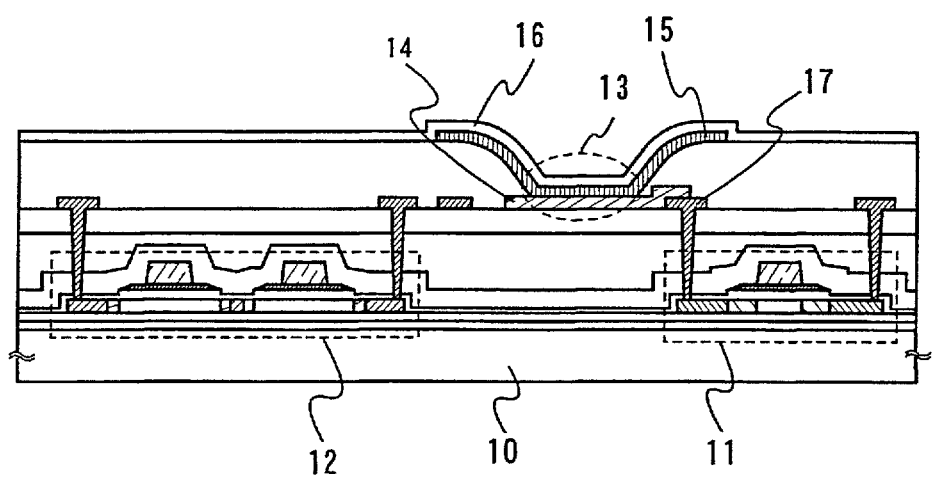
FIG. 4 is a diagram illustrating a light-emitting device.

In the present Embodiment mode, a light-emitting element is manufactured over a substrate 100 composed of glass, quartz, a metal, a bulk semiconductor, transparent plastics, a flexible substrate, or the like. By manufacturing a plurality of light-emitting elements like this over a substrate, a passive matrix light-emitting device can be manufactured. In addition, other than a substrate composed of glass, quartz, transparent plastics, a flexible substrate, or the like, for example, a light-emitting element in contact with a thin film transistor (TFT) array may be manufactured as shown in FIG. 4. In addition, in FIG. 4, a TFT 11 and a TFT 12 are provided over the substrate 100. Then, a light-emitting element 13 is provided in a different layer from TFTs. The light-emitting element 13 includes a layer 15 including a luminescent material between a first electrode 14 and a second electrode 16, and the first electrode 14 and the TFT 11 are electrically connected by a wiring 17. In this way, an active matrix light-emitting device where driving of a light-emitting element is controlled by a TFT can be manufactured. It is to be noted that the structures of the TFTs are not particularly limited. For example, a staggered TFT and an inversely staggered TFT may be used. In addition, the degree of crystallinity of a semiconductor layer forming the TFT is not particularly limited, either. A crystalline semiconductor layer and an amorphous semiconductor layer may be used.

EXAMPLES

Example 1

In the present Example 1, a synthesis example of the organometallic complex (abbreviation: Ir(bfpq)$_2$(acac)) represented by the above structure formula (20) according to the present invention will be described specifically.

[Step 1: Synthesis of Ligand (bfpq)]

First, 3.71 g of 4,4'-fluorobenzil and 1.71 g of o-phenylenediamine were stirred on heating in a solvent (200 mL of chloroform) for 6 hours. The reaction solution was cooled to room temperature, washed with 1 mol/L HCl and a saturated aqueous solution of sodium chloride, and dried with magnesium sulfate. The solvent was removed to obtain a ligand bfpq (2,3-bis(4-fluorophenyl)quinoxaline) (pale yellow powder, yield: 99%).

[Step 2: Synthesis of Dinuclear Complex ([Ir(bfpq)$_2$Cl]$_2$)]

First, with a mixture of 30 ml of 2-ethoxyethanol and 10 ml of water as a solvent, 3.61 g of the ligand Hfdpq (2,3-bis(4-fluorophenyl)quinoxaline) and 1.35 g of iridium chloride (IrCl$_3$.HCl.H$_2$O) were mixed, and held at reflux in a nitrogen atmosphere for 17 hours to obtain a dinuclear complex [Ir(bfpq)$_2$Cl]$_2$ (brown powder, yield: 99%).

[Step 3: Synthesis of Organometallic Compound Ir(bfpq)$_2$(acac) according to the Present Invention]

Further, with 30 ml of 2-ethoxyethanol as a solvent, 2.00 g of the obtained [Ir(bfpq)$_2$Cl]$_2$ obtained, 0.44 ml of acetylacetone (Macao), and 1.23 g of sodium carbonate were mixed, and held at reflux in a nitrogen atmosphere for 20 hours to obtain an organometallic compound Ir(bfpq)$_2$(acac) according to the present invention (red powder, yield: 44%).

In addition, measurement of the thermal decomposition temperature $T_d$ of the obtained organometallic compound Ir(bfpq)$_2$(acac) according to the present invention was performed by a TG-DTA to find $T_d$=365° C., and thus, it is determined that the organometallic complex Ir(bfpq)$_2$(acac) shows favorable heat resistance.

Figure 6:
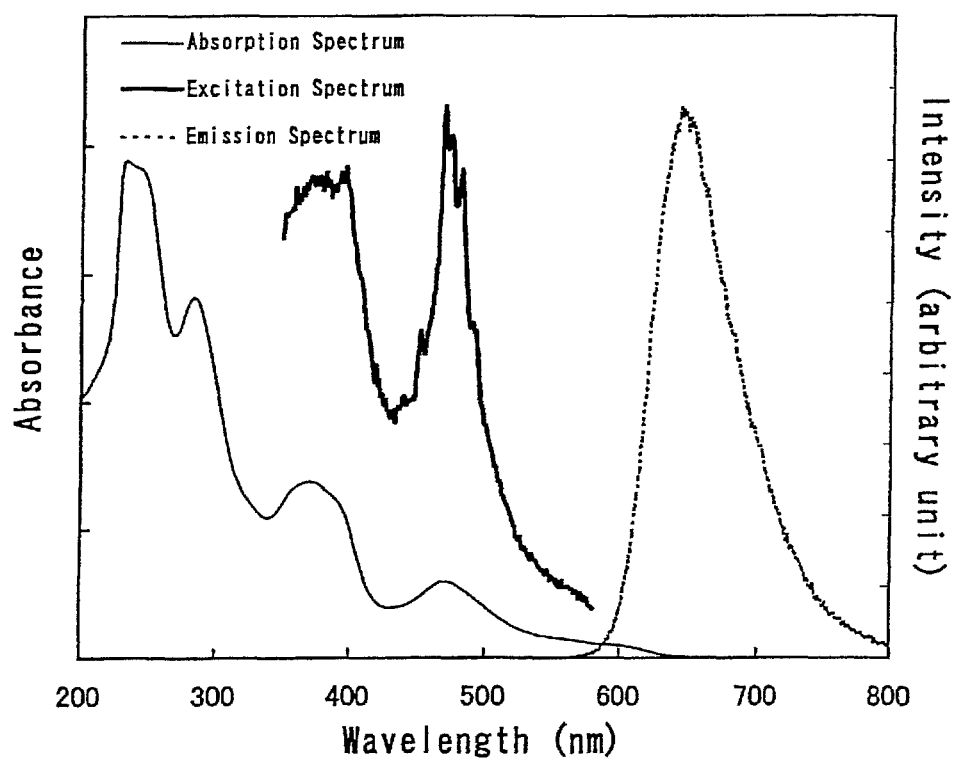
FIG. 6 is a diagram showing an ultraviolet-visible absorption spectrum and a fluorescence spectrum of an organometallic complex according to the present invention.

Next, FIG. 6 shows an absorption spectrum of the obtained Ir(bfpq)$_2$(acac) in dichloromethane and an emission spectrum (PL) thereof. The organometallic compound Ir(bfpq)$_2$(acac) according to the present invention has absorption peaks at 232 nm, 284 nm, 371 nm, and 472 nm. In addition, the emission spectrum shows deep red luminescence with an emission peak at 644 nm.

As descried above, in the case of the organometallic complex Ir(bfpq)$_2$(acac) according to the present invention, the several absorption peaks are observed on the long-wavelength side. This is absorption unique to an organometallic complex as commonly in the case of an orthometalated complex or the like, and is believed to correspond to singlet MLCT transition, triplet π-π* transition, triplet MLCT transition, and the like. In particular, the absorption peak at the longest-wavelength side has a broad peak in the visible region, which is considered to be an absorption spectrum unique to triplet MLCT transition. Namely, it is determined that Ir(bfpq)$_2$(acac) is a compound capable of direct photo-excitation to an excited triplet state and intersystem crossing.

In addition, when a dichloromethane solution of the organometallic complex Ir(bfpq)$_2$(acac) according to the present invention is irradiated with light, luminescence can be observed by argon substitution while luminescence derived from the compound is hardly observed by oxygen substitution, which thing suggests phosphorescence.

Example 2

In the present Example 2, a synthesis example of the organometallic complex (abbreviation:Ir(dpq)$_2$(acac)) a represented by the structure formula (21) according to the present invention will be described specifically.

[Step 1: Synthesis of Dinuclear Complex ([Ir(dpq)$_2$Cl]$_2$)]

First, with a mixture of 30 ml of 2-ethoxyethanol and 10 ml of water as a solvent, 2.36 g of a ligand Hdpq (2,3-diphenylquinoxaline) and 1.00 g of iridium chloride (IrCl$_3$.HCl.H$_2$O) were mixed, and held at reflux in a nitrogen atmosphere for 15 hours to obtain a dinuclear complex [Ir(dpq)$_2$Cl]$_2$ (dark brown powder, yield: 91%).

[Step 2: Synthesis of Organometallic Compound Ir(dpq)$_2$(acac) According to the Present Invention]

Further, with 30 ml of 2-ethoxyethanol as a solvent, 1.00 g of the obtained [Ir(dpq)$_2$Cl]$_2$, 0.20 ml of acetylacetone (Hacac), and 0.67 g of sodium carbonate were mixed, and held at reflux in a nitrogen atmosphere for 15 hours. This was filtered, and the obtained solution was purified by column chromatography with the use of a dichloromethane solvent. Recrystallization was performed with the use of a dichloromethane/ethanol solvent to obtain an organometallic complex Ir(dpq)$_2$(acac) according to the present invention (reddish brown powder, yield: 40%).

In addition, measurement of the thermal decomposition temperature T$_d$ of the obtained organometallic compound Ir(dpq)$_2$(acac) according to the present invention was performed by TG-DTA to find T$_d$=340° C., and thus, it is determined that the organometallic complex Ir(dpq)$_2$(acac) shows favorable heat resistance.

Figure 7:
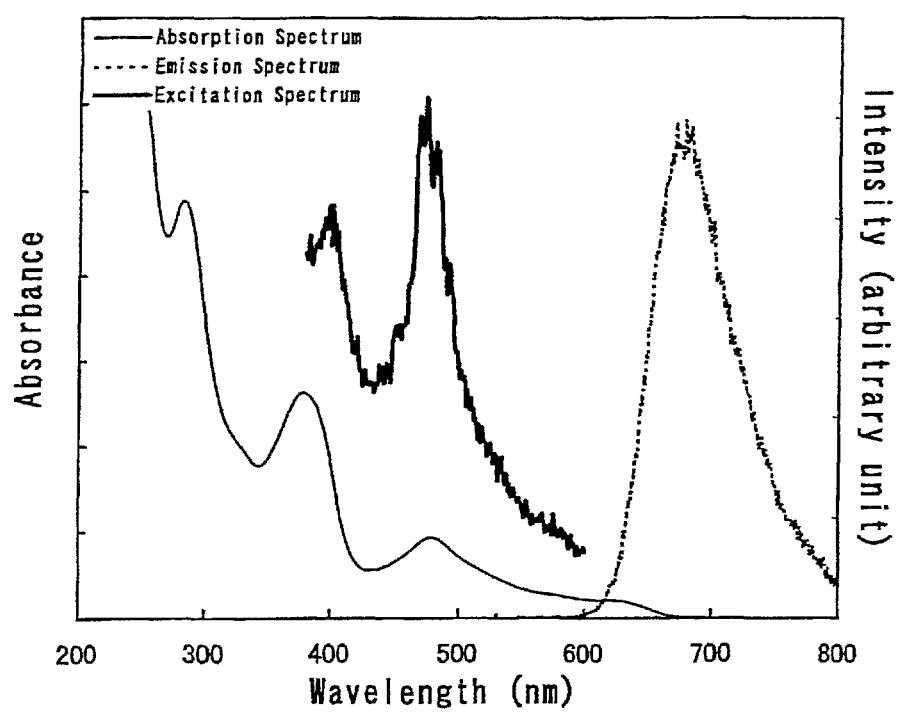
FIG. 7 is a diagram showing an ultraviolet-visible absorption spectrum and a fluorescence spectrum of an organometallic complex according to the present invention.

Next, FIG. 7 shows an absorption spectrum of the obtained Ir(dpq)$_2$(acac) in dichloromethane and an emission spectrum (PL) thereof. The organometallic compound Ir(dpq)$_2$(acac) according to the present invention has absorption peaks at 248 nm, 283 nm, 378 nm, and 479 nm. In addition, the emission spectrum shows deep red luminescence with an emission peak at 687 nm.

As described above in the case of Ir(dpq)$_2$(acac), the several absorption peaks are observed on the high-wavelength side. This is absorption unique to an organometallic complex as commonly in the case of an orthometalated complex or the like, and is believed to correspond to singlet MLCT transition, triplet π-π* transition, triplet MLCT transition, and the like. In particular, the absorption peak at the longest wavelength side has a broad peak in the visible region, which is considered to be an absorption spectrum unique to triplet MLCT transition. Namely, it is determined that Ir(dpq)$_2$(acac) is a compound capable of direct photoexcitation to an excited triplet state and intersystem crossing.

In addition, when a dichloromethane solution of the organometallic complex Ir(dpq)$_2$(acac) according to the present invention is irradiated with light, luminescence can be observed by argon substitution method while luminescence derived from the compound is hardly observed by oxygen substitution method, which thing suggest phosphorescence.

Example 3

Figure 8:
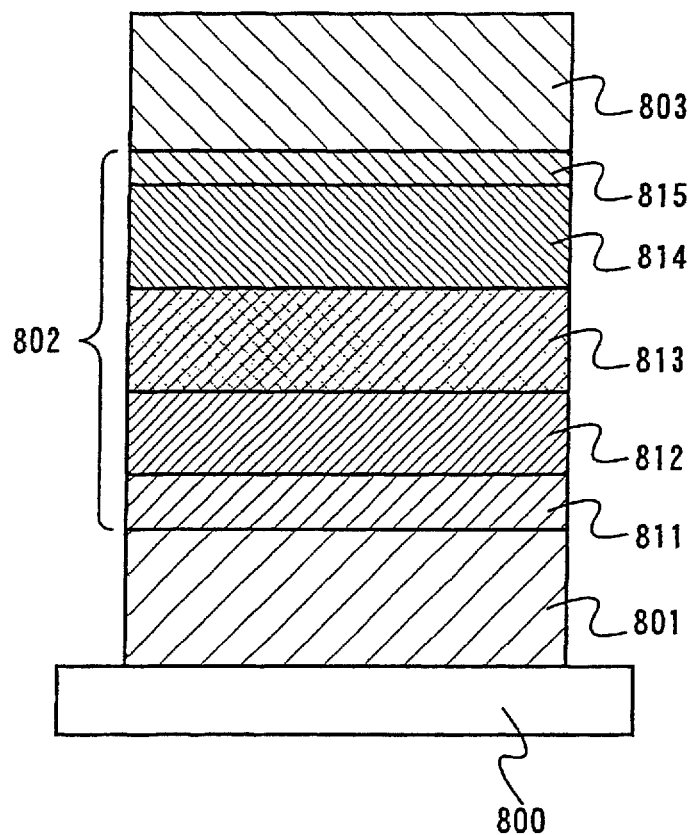
FIG. 8 is a diagram illustrating the structure of a light-emitting element using an organometallic complex according to the present invention.

In the present example, in the case of manufacturing a light-emitting element by using an organometallic complex according to the present invention for a part of a layer included luminescence material, specifically, an element structure in the case of using an organometallic complex according to the present invention as a guest material for a light-emitting layer will be described with reference to FIG. 8.

First, on a substrate 800, a first electrode 801 was formed. It is to be noted that the first electrode 801 functions as an anode in the present Example. An ITO that was a transparent conductive film was used as a material and deposited by sputtering to be 110 nm in film thickness.

Next, on the first electrode 801 (anode), a layer 802 including a luminescent material was formed. It is to be noted that the layer 802 including the luminescent material in the present Example has a laminated structure composed of a hole injecting layer 811, a hole transporting layer 812, a light-emitting layer 813, an electron transporting layer 814, and an electron injecting layer 816.

The hole injecting layer 811 was formed to be 20 nm in film thickness by evaporation using resistance heating in such a way that the substrate on which the first electrode 801 was formed was fixed in a substrate holder of a commercially produced vacuum deposition system with the surface at which the first electrode 801 was formed down and copper phthalocyanine (hereinafter, referred to as Cu-Pc) was put in an evaporation source provided in the vacuum deposition system. Further, known hole injecting materials can be used as a material forming the hole injecting layer 811.

Next, the hole transporting layer 812 is formed by using a material that has an excellent hole transporting property. Known hole transporting materials can be used as a material forming the hole transporting layer 812, however, in the present example, α-NPD was deposited to be 40 nm in film thickness in a similar way.

Next, the light-emitting layer 813 is formed. It is noted that a hole and an electron are recombined in the layer 813 to produce luminescence. The light-emitting layer 813 formed in conact with the hole transporting layer 812 was formed by using a host material and a guest material that is an organometallic complex according to the present invention.

Specifically, TPAQn as the host material and Ir(bfq)$_2$(acac) as the guest material were used, and deposited by co-evaporation to be 30 nm in film thickness. The rate of the guest material was made to be 8.7%.

Next, the electron transporting layer 814 is formed. Known electron transporting material can be used as a materials forming the electron transporting layer 814, however, in the present Example, Alq$_3$ was deposited by evaporation to be 30 nm in film thickness.

Next, the electron injecting layer 815 was formed. Known electron injecting materials can be used as a material forming the electron injecting layer 815, however, in the present example, calcium fluoride (hereinafter, referred to as CaF$_2$) was used, and deposited by evaporation to be 2 nm in film thickness.

As described above, after forming the layer 802 including the luminescent material formed by stacking the hole injecting layer 811, the hole transporting layer 812, the light-emitting layer 813, the electron transporting layer 814, and the electron injecting layer 815, the second electrode 803 to function as a cathode was formed by sputtering or evaporation. Further, in the present example, the second electrode 803 was obtained by forming aluminum (150 nm) on the layer 802 including the luminescent material by evaporation.

As the described, the light-emitting element using the organometallic complex according to the present invention was formed.

Furthermore, when a voltage is applied to the formed light-emitting element, in the case of the light-emitting element, red luminescence was observed at a voltage of 4.0 V or more and a luminance of 466 cd/m$^2$ was observed at a voltage of 7.6 V. The luminous efficiency was 1.56 cd/A in that case. Further, the peak wavelength of an emission spectrum is 652 nm, which shows favorable red luminescence.

Further, the CIE chromaticity coordinates in this case were (x, y)=(0.65, 0.33).

Example 4

In the present example, a light-emitting device that has a light-emitting element according to the present invention in a pixel portion will be described with reference to FIG. 9. FIG. 9A is a top view showing the light-emitting device and FIG. 9B is a cross-sectional view taken along the line A-A' in FIG. 9A. Reference numeral 601 indicated by a dotted line denotes a driver circuit portion (a source side driver circuit), reference numeral 602 denotes a pixel portion, and reference numeral 603 denotes a driver circuit portion (a gate side driver circuit). In addition, reference numerals 604 and 605 denote a sealing substrate and a sealing material, respectively. The inside surrounded by the sealing material 605 is a space 607.

Further, reference numeral 608 denotes a wiring for transmitting signals to be input to the source side driver circuit 601 and the gate side driver circuit 603, and receives signals such as a video signal, a clock signal, a start signal, and a reset signal from an FPC (Flexible Printed Circuit) 609 that serves as an external input terminal. It is to be noted that although only the FPC is shown in the figure here, a printed wiring board (PWB) may be attached to this FPC. The light-emitting device in this specification includes not only a light-emitting device body but also a state in which an FPC or a PWB is attached thereto.

Next, the sectional structure will be described with reference to FIG. 9B. Although the driver circuit portion and the pixel portion are formed over an element substrate 610, the source side driver circuit 601 as the driver circuit portion and the pixel portion 602 are shown here.

In the source side driver circuit 601, a CMOS circuit is formed by a combination of an n-channel TFT 623 and a p-channel TFT 624. The TFTs forming the driver circuit may be formed by a known CMOS circuit, PMOS circuit, or NMOS circuit. Although the present example shows a driver integrated type in which a driver circuit is formed over a substrate, which is not always necessary, the driver circuit can be formed not over the substrate but outside the substrate.

The pixel portion 602 has a plurality of pixels, each including a switching TFT 611, a current controlling TFT 612, and a first electrode 613 electrically connected to a drain of the controlling TFT 613. Further, an insulator 614 is formed to cover an edge of the first electrode 613. Here, a positive photosensitive acrylic resin film is used to form the insulator 614.

Besides, in order to obtain a favorable coverage, the insulator 614 is formed to have a top portion or a bottom potion with a curved surface that has a curvature. For example, in the case of using positive photosensitive acrylic as a material for the insulator 614, it is preferable that only a top portion of the insulator 614 have a curved surface with a curvature radius (0.2 to 3 µm). In addition, any of a negative photosensitive material that becomes insoluble in an etchant by light and a positive photosensitive material that becomes soluble in an etchant by light can be used for the insulator 614.

On the first electrode 613, a layer 616 including a luminescent material and a second electrode 617 are formed. Here, as a material to be used for the first electrode 613 that functions as an anode, it is preferable to use a material that has a large work function. For example, in addition to single layers such as an ITO (indium tin oxide) film, a ITSO (indium tin oxide containing silicon oxide), an indium zinc oxide (IZO) film, a titanium nitride film, a chromium film, a tungsten film, a Zn film, and a Pt film, a lamination layer of titanium nitride and a film including aluminum as its main component and a three-layer structure of a titanium nitride film, a film including aluminum as its main component, and a titanium nitride film, and the like can be used. When a laminated structure is used, it is possible to have a lower resistance as a wiring, take favorable ohmic contact, and function as an anode.

In addition, the layer 616 including the luminescent material is formed by evaporation using an evaporation mask or by inkjet. The layer 616 including the luminescent material includes an organometallic complex according to the present invention. As a material to be used in combination with these organometallic complexes, low molecular weight materials, middle molecular weight materials (including an oligomer and a dendrimer) or polymer materials may be used. In addition, as a material to be used for the layer including the luminescent material, it is often the case that an organic material is used for a single layer or a lamination layer. However, the present invention includes a structure in which an inorganic compound is used for a part of a film composed of an organic compound.

Further, as a material to be used for the second electrode (cathode) 617 formed on the layer 616 including the luminescent material, a material that has a small work function (Al, Ag, Li, or Ca, an alloy thereof such as MgAg, MgIn, or AlLi, $CaF_2$ or CaN) may be used. In the case of transmitting light generated in the layer 616 including the luminescent material through the second electrode 617, it is preferable to use a lamination layer of a metal thin film that has a thinned film thickness and a transparent conductive film (for example, an ITO (an alloy of indium oxide and tin oxide), an ally of indium oxide and zinc oxide ($In_2O_3$—ZnO), or zinc oxide (ZnO)) as the second electrode (cathode) 617.

Further, the sealing substrate 604 and the element substrate 610 are bonded with the sealing material 605 to have a structure where a light-emitting element 618 is provided in the space 607 surrounded by the element substrate 610, the sealing substrate 604, and the sealing material 605. The space 607 also includes a structure of filling with the sealing material 605 in addition to a case of filling with an inert gas (for example, nitrogen or argon).

It is to be noted that it is preferable to use an epoxy resin for the sealing material 605. In addition, it is desirable to use a material that allows permeation of moisture or oxygen as little as possible. Further, as a material to be used for the sealing substrate 604, a plastic substrate composed of FRP (Fiber-glass-Reinforced Plastics), PVF (polyvinylfluoride), Mylar, polyester, acrylic, or the like can be used besides a glass substrate and a quarts substrate.

As described above, a light-emitting device that has a light-emitting element according to the present invention can be obtained. In the light-emitting device to which the present invention is applied, the light-emitting element according to the present invention emits phosphorescence, and is excellent in luminous efficiency. Therefore, the light-emitting device consumes low power.

Further, the light-emitting device in the present example can be implemented freely in combination with the structure of the light-emitting element described in Example 3. In addition, for the light-emitting device described in the present Example, a chromaticity converting film such as a color filter may be used as necessary.

Moreover, various electric apparatuses completed by using a light-emitting device that has a light-emitting element according to the present invention will be described. Since a light-emitting device to which the present invention is applied has a characteristic of low power consumption, an electronic device using the light-emitting device can reduce, for example, power for a display portion.

Electric apparatus manufactured by using a light-emitting device formed according to the present invention include a television, a camera such as a video camera and a digital camera, a goggle-type display (head mount display), a navigation system, a sound reproduction device (such as an in-car audio system or an audio set), a personal computer, a game machine, a personal digital assistance (such as a mobile computer, a cellular phone, a portable game machine, or an electronic book), and an image reproduction device equipped with a recording medium (specifically, a device equipped with a display device, which can reproduce a recording medium such as a digital versatile disc (DVD) and display the image). Specific examples of these electric apparatuses will be shown in FIG. 10.

Figure 10:
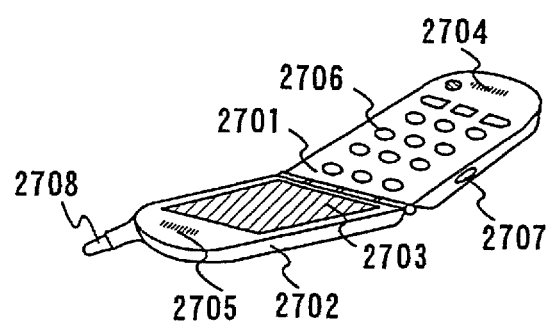
FIG. 10 is a diagram illustrating electronic devices to which the present invention is applied.

Here, FIG. 10 is a cellular phone, which includes a main body 2701, a frame body 2702, a display portion 2703, a voice input portion 2704, a voice output portion 2705, an operation key 2706, an external connection port 2707, and an antenna 2708. A light-emitting device that has a light-emitting element according to the present invention is used for the display portion 2703 to manufacture the cellular phone.

As an electronic device that needs charging, such as a cellular phone in particular, reducing power for a display portion makes it possible to use the electronic device for a longer stretch of time after charging.

What is claimed is:

1. A light-emitting element comprising:

an organometallic complex comprising a structure represented by the following formula (1),

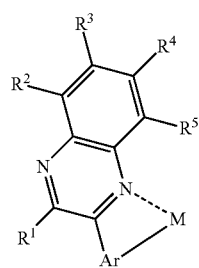

(1)

wherein each of $R^1$ to $R^5$ comprises any one selected from the group of hydrogen, a halogen, an alkyl group, an alkoxy group, an aryl group and a cyano group, wherein Ar comprises an aryl group, and wherein M comprises an element of Group 9 or 10.

2. The light-emitting element according to claim 1, wherein the M is an iridium atom or a platinum atom.

3. The light-emitting element according to claim 1, wherein further comprising a light-emitting layer including the organometallic complex.

4. The light-emitting element according to claim 1, wherein the organometallic complex is included in a light-emitting layer as a guest material, and wherein a quinoxaline derivative is included in the light-emitting layer as a host material.

5. A light-emitting element comprising:

an organometallic complex comprising a structure represented by the following formula (2),

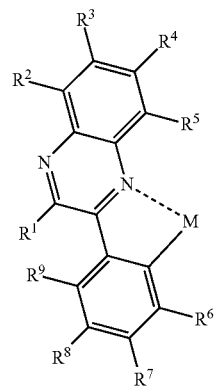

(2)

wherein each of $R^1$ to $R^9$ comprises any one selected from the group of hydrogen, a halogen, an alkyl group, an alkoxy group, an aryl group, and a cyano group, and wherein M comprises an element of Group 9 or 10.

6. The light-emitting element according to claim 5, wherein the M is an iridium atom or a platinum atom.

7. The light-emitting element according to claim 5, further comprising a light-emitting layer including the organometallic complex.

8. The light-emitting element according to claim 5, wherein the organometallic complex is included in a light-emitting layer as a guest material, and wherein a quinoxaline derivative is included in the light-emitting layer as a host material.

9. A light-emitting element comprising:

an organometallic complex represented by the following formula (3),

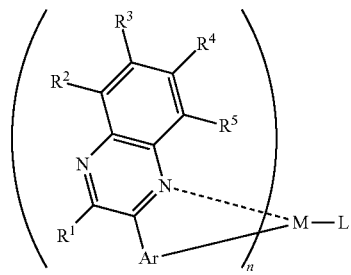

(3)

wherein each of $R^1$ to $R^5$ comprises any one selected from the group of hydrogen, a halogen, an alkyl group, an alkoxy group, an aryl group, and a cyano group, wherein Ar comprises an aryl group, wherein M comprises an element of Group 9 or an element of Group 10, wherein n is 2 when the M comprises the element of Group 9 while n is 1 when the M comprises the element of Group 10, and wherein L comprises any one of a monoanionic ligand having a β-diketone structure, a monoanionic bidentate chelate ligand having a carboxyl group, and a monoanionic bidentate chelate ligand having a phenolic hydroxyl group.

10. The light-emitting element according to claim 9, wherein the L is any one of monoanionic bidentate chelate ligands shown by the following structure formulas (5) to (11).

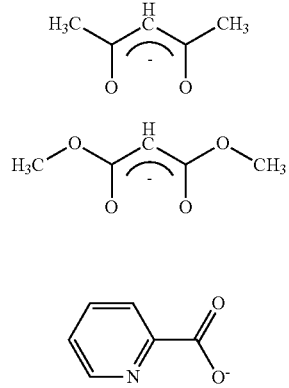

(5)

(6)

(7)

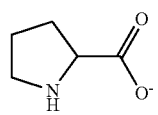

(8)

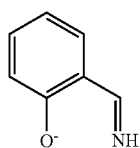

(9)

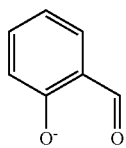

(10)

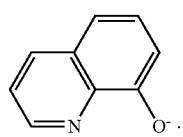

(11)

11. The light-emitting element according to claim 9 or 10, wherein the M is an iridium atom or a platinum atom.

12. The light-emitting element according to claim 9 or 10, further comprising a light-emitting layer including the organometallic complex.

13. The light-emitting element according to claim 9 or 10, wherein the organometallic complex is included in a light-emitting layer as a guest material, and
wherein a quinoxialine quinoxaline derivative is included in the light-emitting layer as a host material.

14. A light-emitting element comprising:
an organometallic complex represented by the following formula (4),

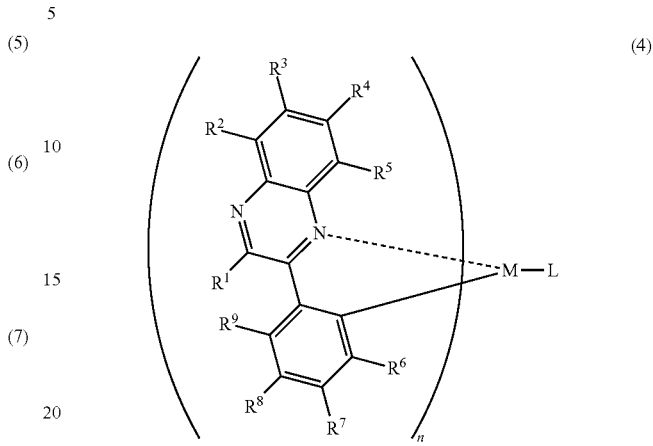

(4)

wherein each of $R^1$ to $R^9$ comprises any one selected from the group of hydrogen, a halogen, an alkyl group, an alkoxy group, an aryl group, and a cyano group, wherein M comprises an element of Group 9 or an element of Group 10, wherein n is 2 when the M comprises the element of Group 9 while n is 1 when the M comprises the element of Group 10, and wherein L comprises any one of a monoanionic ligand having a β-diketone structure, a monoanionic bidentate chelate ligand having a carboxyl group, and a monoanionic bidentate chelate ligand having a phenolic hydroxyl group.

15. The light-emitting element according to claim 14, wherein the L is any one of monoanionic bidentate chelate ligands shown by the following structure formulas (5) to (11)

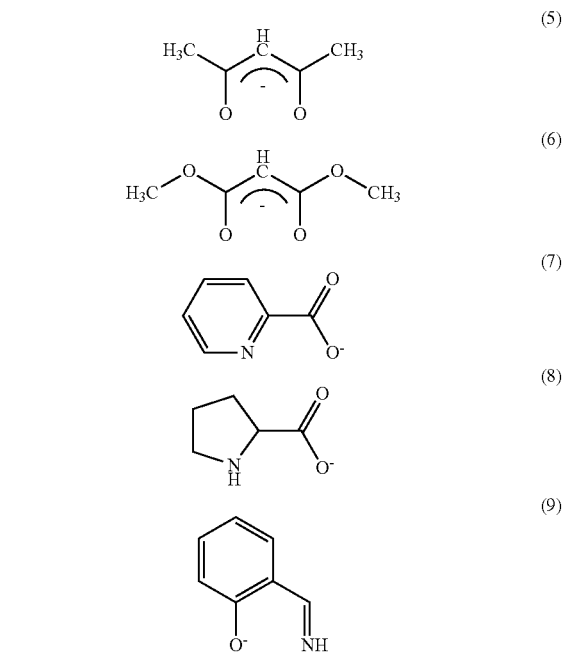

(5)

(6)

(7)

(8)

(9)

-continued (10)

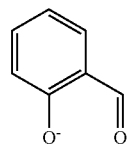

(11)

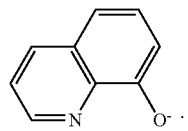

16. The light-emitting element according to claim 14 or 15, wherein the M is an iridium atom or a platinum atom.

17. The light-emitting element according to claim 14 or 15, further comprising a light-emitting layer including the organometallic complex.

18. The light-emitting element according to claim 14 or 15, wherein the organometallic complex is included in a light-emitting layer as a guest material, and
wherein a quinoxaline derivative is included in the light-emitting layer as a host material.

19. A light-emitting element comprising:
an organometallic complex comprising a structure represented by the following formula (12), (12)

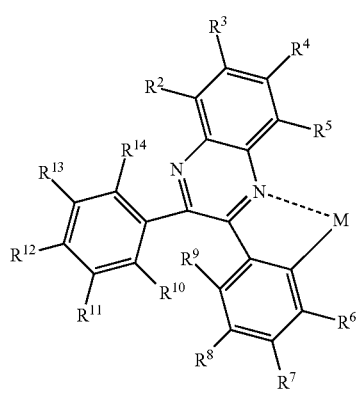

wherein each of $R^2$ to $R^{14}$ comprises any one selected from the group of hydrogen, a halogen, an alkyl group, an alkoxy group, an aryl group, and a cyano group, and
wherein M is an element of Group 9 or 10.

20. The light-emitting element according to claim 19, wherein the M is an iridium atom or a platinum atom.

21. The light-emitting element according to claim 19, further comprising a light-emitting layer including the organometallic complex.

22. The light-emitting element according to claim 19, wherein the organometallic complex is included in a light-emitting layer as a guest material, and
wherein a quinoxialino quinoxaline derivative is included in the light-emitting layer as a host material.

23. A light-emitting element comprising:
an organometallic complex comprising a structure represented by the following formula (13), (13)

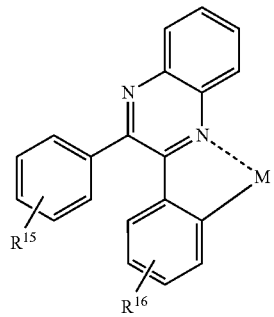

wherein $R^{15}$ or $R^{16}$ comprises any one selected from the group of hydrogen, a halogen, and a haloalkyl group, and
wherein M comprises an element of Group 9 or 10.

24. The light-emitting element according to claim 23, wherein the M is an iridium atom or a platinum atom.

25. The light-emitting element according to claim 23, further comprising a light-emitting layer including the organometallic complex.

26. The light-emitting element according to claim 23, wherein the organometallic complex is included in a light-emitting layer as a guest material, and
wherein a quinoxaline derivative is included in the light-emitting layer as a host material.

27. A light-emitting element comprising:
an organometallic complex represented by the following formula (14), (14)

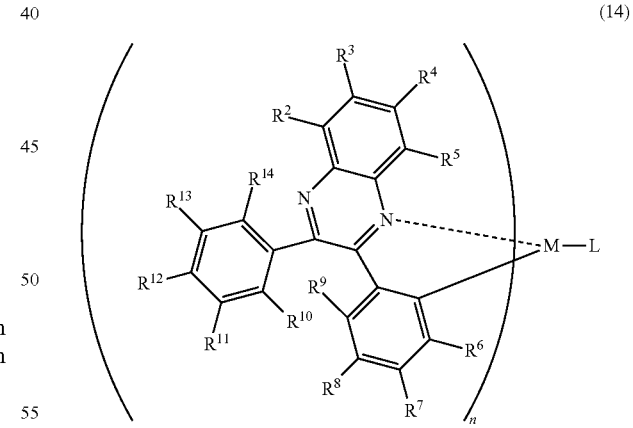

wherein each of $R^2$ to $R^{14}$ comprises any one selected from the group of hydrogen, a halogen, an alkyl group, an alkoxy group, an aryl group, and a cyano group,
wherein M comprises an element of Group 9 or an element of Group 10,
wherein n is 2 when the M comprises the element of Group 9 while n is 1 when the M comprises the element of Group 10, and
wherein L comprises any one of a monoanionic ligand having a β-diketone structure, a monoanionic bidentate chelate ligand having a carboxyl group, and a monoanionic bidentate chelate ligand having a phenolic hydroxyl group.

28. The light-emitting element according to claim 27, wherein the L is any one of monoanionic bidentate chelate ligands shown by the following structure formulas (5) to (11)

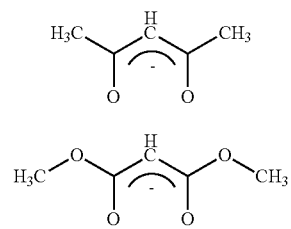

(5)

(6)

(7)

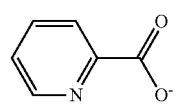

(8)

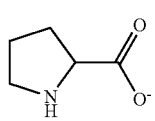

(9)

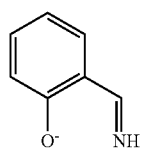

(10)

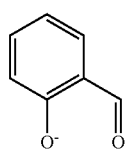

(11)

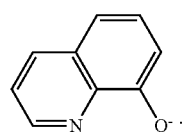

29. The light-emitting element according to claim 27 or 28, wherein the M is an iridium atom or a platinum atom.

30. The light-emitting element according to claim 27 or 28, further comprising a light-emitting layer including the organometallic complex.

31. The light-emitting element according to claim 27 or 28, wherein the organometallic complex is included in a light-emitting layer as a guest material, and
wherein a quinoxaline derivative is included in the light-emitting layer as a host material.

32. A light-emitting element having an organometallic complex represented by the following formula (15), (15)

[Structure showing quinoxaline-phenyl complex with $R^{15}$ and $R^{16}$ substituents, M—L, subscript n]

wherein $R^{15}$ or $R^{16}$ comprises any one selected from the group of hydrogen, a halogen, and a haloalkyl group, wherein M comprises an element of Group 9 or an element of Group 10, wherein n is 2 when the M comprises the element of Group 9 while n is 1 when the M comprises the element of Group 10, and wherein L comprises any one of a monoanionic ligand having a β-diketone structure, a monoanionic bidentate chelate ligand having a carboxyl group, and a monoanionic bidentate chelate ligand having a phenolic hydroxyl group.

33. The light-emitting element according to claim 32, wherein the L is any one of monoanionic bidentate chelate ligands shown by the following structure formulas (5) to (11)

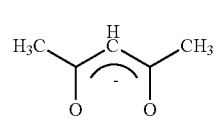

(5)

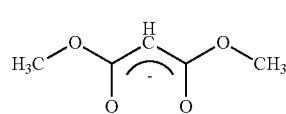

(6)

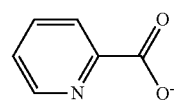

(7)

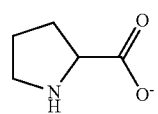

(8)

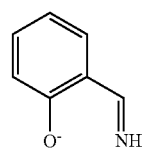

(9)

(10)

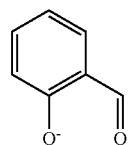

(11)

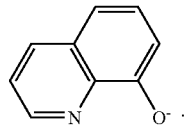

34. The light-emitting element according to claim 32 or 33, wherein the M is an iridium atom or a platinum atom.

35. The light-emitting element according to claim 32 or 33, further comprising a light-emitting layer including the organometallic complex.

36. The light-emitting element according to claim 32 or 33, wherein the organometallic complex is included in a light-emitting layer as a guest material, and
    wherein a quinoxaline derivative is included in the light-emitting layer as a host material.

* * * * *

UNITED STATES PATENT AND TRADEMARK OFFICE
CERTIFICATE OF CORRECTION

PATENT NO.        : 8,569,486 B2
APPLICATION NO.   : 13/609970
DATED             : October 29, 2013
INVENTOR(S)       : Hideko Inoue et al.

It is certified that error appears in the above-identified patent and that said Letters Patent is hereby corrected as shown below:

In the Specifications

At column 29, line 17, "matcrial of material of," should be --material of--;

At column 29, line 31, "BAIq)," should be --Balq),--;

At column 32, line 29, "(Macao)" should be --(Hacac)--;

In the Claims

In claim 3, at column 37, line 60, please delete "wherein";

In claim 13, at column 39, line 66, "quinoxialinc quinoxaline" should be --quinoxaline--;

In claim 22, at column 41, line 66, "quinoxialino quinoxaline" should be --quinoxaline--.

Signed and Sealed this
Twenty-ninth Day of April, 2014

Michelle K. Lee
*Deputy Director of the United States Patent and Trademark Office*